(12) United States Patent
Laniado et al.

(10) Patent No.: US 11,742,057 B2
(45) Date of Patent: Aug. 29, 2023

(54) SYSTEMS AND METHODS FOR ARTIFICIAL INTELLIGENCE-BASED PREDICTION OF AMINO ACID SEQUENCES AT A BINDING INTERFACE

(71) Applicant: Pythia Labs, Inc., Los Angeles, CA (US)

(72) Inventors: Joshua Laniado, Los Angeles, CA (US); Julien Jorda, Los Angeles, CA (US); Matthias Maria Alessandro Malago, Santa Monica, CA (US); Thibault Marie Duplay, Los Angeles, CA (US); Mohamed El Hibouri, Los Angeles, CA (US); Lisa Juliette Madeleine Barel, Los Angeles, CA (US); Ramin Ansari, Los Angeles, CA (US)

(73) Assignee: Pythia Labs, Inc., Los Angeles, CA (US)

( * ) Notice: Subject to any disclaimer, the term of this patent is extended or adjusted under 35 U.S.C. 154(b) by 0 days.

(21) Appl. No.: 17/871,425

(22) Filed: Jul. 22, 2022

(65) Prior Publication Data

US 2023/0040576 A1 Feb. 9, 2023

Related U.S. Application Data

(63) Continuation-in-part of application No. 17/384,104, filed on Jul. 23, 2021, now Pat. No. 11,450,407.

(Continued)

(51) Int. Cl.
*G16B 15/30* (2019.01)
*G16B 45/00* (2019.01)
*G16B 40/00* (2019.01)

(52) U.S. Cl.
CPC ............. *G16B 15/30* (2019.02); *G16B 40/00* (2019.02); *G16B 45/00* (2019.02)

(58) Field of Classification Search
CPC ..... G16B 15/30; G16B 40/00; C12N 15/1089
See application file for complete search history.

(56) References Cited

U.S. PATENT DOCUMENTS

| 5,526,281 A | 6/1996 | Chapman et al. |
| 9,296,802 B2 * | 3/2016 | Choi ........................ C07K 1/00 |

(Continued)

FOREIGN PATENT DOCUMENTS

| EP | 3739589 A1 | 11/2020 |
| KR | 20210145059 A * | 12/2021 |

(Continued)

OTHER PUBLICATIONS

ArXiv: 1905.13639 for Lim, Jaechang, et al. "Scaffold-based molecular design with a graph generative model." [Submitted on May 31, 2019] (Year: 2019).*

(Continued)

*Primary Examiner* — Jesse P Frumkin
(74) *Attorney, Agent, or Firm* — Choate, Hall & Stewart LLP; Ronen Adato; William R. Haulbrook

(57) ABSTRACT

Presented herein are systems and methods for prediction of protein interfaces for binding to target molecules. In certain embodiments, technologies described herein utilize graph-based neural networks to predict portions of protein/peptide structures that are located at an interface of custom biologic (e.g., a protein and/or peptide) that is being designed for binding to a target molecule, such as another protein or peptide. In certain embodiments, graph-based neural network models described herein may receive, as input, a representation (e.g., a graph representation) of a complex comprising a target and a partially-defined custom biologic.

(Continued)

Portions of the partially-defined custom biologic may be known, while other portions, such an amino acid sequence and/or particular amino acid types at certain locations of an interface, are unknown and/or to be customized for binding to a particular target. A graph-based neural network model as described herein may then, based on the received input, generate predictions of likely acid sequences and/or types of particular amino acids at the unknown portions. These predictions can then be used to determine (e.g., fill in) amino acid sequences and/or structures to complete the custom biologic.

30 Claims, 21 Drawing Sheets

Related U.S. Application Data

(60) Provisional application No. 63/353,481, filed on Jun. 17, 2022, provisional application No. 63/224,801, filed on Jul. 22, 2021, provisional application No. 63/224,801, filed on Jul. 22, 2021.

(56) References Cited

U.S. PATENT DOCUMENTS

| | | | |
|---|---|---|---|
| 9,373,059 B1 | 6/2016 | Heifets et al. | |
| 11,256,994 B1* | 2/2022 | Bucher | G06V 20/69 |
| 11,450,407 B1 | 9/2022 | Laniado et al. | |
| 2002/0072864 A1* | 6/2002 | Lacroix | C07K 1/00 702/19 |
| 2002/0133297 A1 | 9/2002 | Yang et al. | |
| 2002/0147547 A1* | 10/2002 | Desjarlais | C07K 1/00 703/11 |
| 2004/0199334 A1 | 10/2004 | Kovesdi et al. | |
| 2012/0239367 A1 | 9/2012 | Tong et al. | |
| 2013/0330335 A1 | 12/2013 | Bremel et al. | |
| 2016/0300127 A1 | 10/2016 | Heifets et al. | |
| 2018/0260517 A1 | 9/2018 | Blattner et al. | |
| 2018/0285731 A1 | 10/2018 | Heifets et al. | |
| 2018/0341754 A1 | 11/2018 | Fan et al. | |
| 2019/0272887 A1 | 9/2019 | Feinberg et al. | |
| 2020/0342953 A1 | 10/2020 | Morrone et al. | |
| 2021/0304847 A1 | 9/2021 | Senior et al. | |
| 2022/0165366 A1* | 5/2022 | Zubarev | G16C 20/30 |
| 2022/0375538 A1* | 11/2022 | Das | G16B 15/20 |
| 2023/0022022 A1 | 1/2023 | Laniado et al. | |
| 2023/0034425 A1 | 2/2023 | Laniado et al. | |
| 2023/0083810 A1* | 3/2023 | Xu | G16C 20/90 703/11 |

FOREIGN PATENT DOCUMENTS

| | | |
|---|---|---|
| WO | WO-2013/040142 A2 | 3/2013 |
| WO | WO-2018/213767 A1 | 11/2018 |
| WO | WO-2020/123302 A1 | 6/2020 |
| WO | WO-2023/004116 A1 | 1/2023 |

OTHER PUBLICATIONS

Lim, Jaechang, et al. "Scaffold-based molecular design with a graph generative model." Chemical science 11.4 (2020): 1153-1164. (Year: 2020).*
Machine translation of KR20210145059A (Scaffold-based molecular design with a graph generative model); translated document form IP.com (Year: 2021).*
Ashtawy, Hossam Mohamed Farg., A Comparative Study of Machine-learning-based Scoring Functions in Predicting Protein-ligand Binding Affinity. Michigan State University. Electrical Engineering, 149 pages, (2011).
Cao, L. et. al., De novo design of picomolar SARS-CoV-2 miniprotein inhibitors, Science, 370(6515):426-431, (2020).
Chevalier, A., et. al., Massively parallel de novo protein design for targeted therapeutics, Nature 550:74-79, (2017).
Collaborative Computational Project, No. 4, The CCP4 Suite: Programs for Protein Crystallography, Acta Crystallogr D Biol Crystallogr. D50:760-763 (1994).
Dauparas, J. et al., Robust deep learning based protein sequence design using ProteinMPNN, bioRxiv preprint, 33 pages, (2022).
Dhariwal, P. and Nichol, A., Diffusion models beat GANs on image synthesis, arXiv preprint, 44 pages, (2021).
Gorski, K.M., et. al., HEALPix—a Framework for high resolution discretization, and fast analysis of data distributed on the sphere, 622:759-771, (2005).
Hassan-Harrirou, H., et. al., RoSENet: Improving Binding Affinity Prediction by Leveraging Molecular Mechanics Energies with an Ensemble of 3D Convolutional Neural Networks, J. Chem. Inf. Model, 60(6):2791-2802, (2020).
Hsu, C. et al., Learning inverse folding from millions of predicted structures, bioRxiv preprint, 22 pages, (2022).
Ingraham, J. et al., Generative Models for Graph-Based Protein Design, 33rd Conference on Neural Information Processing Systems (NeurIPS 2019), Vancouver, Canada, 12 pages, (2019). Retrieved online at: <https://proceedings.neurips.cc/paper/2019/hash/f3a4ff4839c56a5f460c88cce3666a2b-Abstract.html>.
Jiménez, J. et. al., KDEEP: Protein-Ligand Absolute Binding Affinity Prediction via 3D-Convolutional Neural Networks, J. Chem. Inf. Model, 58(2):287-296, (2018).
Liu, Y. et al., Rotamer-free protein sequence design based on deep learning and self-consistency, Nature Computational Science, 19 pages, (2022).
McPartlon, M. et al., A deep SE(3)-equivariant model for learning inverse protein folding, bioRxiv preprint, 18 pages, (2022).
Pierce, B.G., et.al., Accelerating Protein Docking in ZDOCK Using an Advanced 3D Convolution Library, PLoS ONE, e24657, 6(9):1-6, (2011).
Ragoza, M. et. al., Protein-Ligand Scoring with Convolutional Neural Networks, J. Chem. Inf. Model, 57(4):942-957, (2017).
Shapovalov, M.S., and Dunbrack, R.L., Jr., A smoothed backbone-dependent rotamer library for proteins derived from adaptive kernel density estimates and regressions, Structure, 19(6):844-858, <https://www.cell.com/structure/fulltext/S0969-2126(11)00144-4> (2011).
Strokach, A. et al., Fast and Flexible Protein Design Using Deep Graph Neural Networks, Cell Syst., 11(4):402-411, (2020).
The CCP4 Suite, Computer programs for protein crystallography, Overview and Manual, 130 pages, Feb. 2006
Wallach, I., et. al., AtomNet: A Deep Convolutional Neural Network for Bioactivity Prediction in Structure-based Drug Discovery, 1-11, (2015).
Winn, M.D., et. al., Overview of the CCP4 suite and current developments, Acta Crystallogr. Section D, Biological Crystallography, ISSN 0907-4449, D67:235-242, (2011).
Yang, J. et al., Improved protein structure prediction using predicted interresidue orientations, Proc. Natl. Acad. Sci. USA, 117(3):1496-1503, (2020).
Yang, K. et al., Masked inverse folding with sequence transfer for protein representation learning, bioRxiv preprint, 16 pages, (2022).
Yershova, A., et. al., Generating uniform incremental grids on SO(3) Using the Hopf Fibration, The Internation Journal of Robotics Research, 29:(7):801-812, (2010).
Zhang, Z. et al., Protein representation learning by geometric structure pretraining, arXiv preprint, 25 pages, (2022).
Satorras, V.G. et al., E(n) Equivariant Graph Neural Networks, Proc. 38th Int. Conf. Machine Learning, PMLR, 139, 10 pages, (2021).
Shrake, A. and Rupley, J.A., Environment and exposure to solvent of protein atoms. Lysozyme and insulin, J. Mol. Biol., 79(2):351-371 (1973).
International Search Report for PCT/US2022/038014, filed Jul. 22, 2022, 4 pages, (dated Nov. 15, 2022).
Senior, A.W. et al., Protein structure prediction using multiple deep neural networks in the 13th Critical Assessment of Protein Structure Prediction (CASP13), Proteins, 87(12):1141-1148 (2019).
Tien, M.Z. et al., Maximum allowed solvent accessibilites of residues in proteins, PLoS One, 8(11):e80635 (2013), 8 pages.

(56) References Cited

OTHER PUBLICATIONS

Written Opinion for PCT/US2022/038014, filed Jul. 22, 2022, 8 pages, (dated Nov. 15, 2022).
Gainza, P. et al., De novo design of site-specific protein interactions with learned surface fingerprints, bioRxiv preprint, 41 pages, (2022).
Gainza, P. et al., Deciphering interaction fingerprints from protein molecular surfaces using geometric deep learning, Nat. Methods, 17(2):184-192 (2020).
Anand, N. et al., Protein Sequence Design With A Learned Potential, bioRxiv 2020.01.06.895466; 23 pages, (2020), doi: https://doi.org/10.1101/2020.01.06.895466.
Lipman, Y. et al., Flow Matching for Generative Modeling, arXiv Preprint, available online at https://arxiv.org/abs/2210.02747v1, 24 pages, (Oct. 6, 2022).
Vaswani, A. et al., Attention Is All You Need, arXiv Preprint, available online at https://arxiv.org/abs/1706.03762, 15 pages, (Dec. 6, 2017).

\* cited by examiner

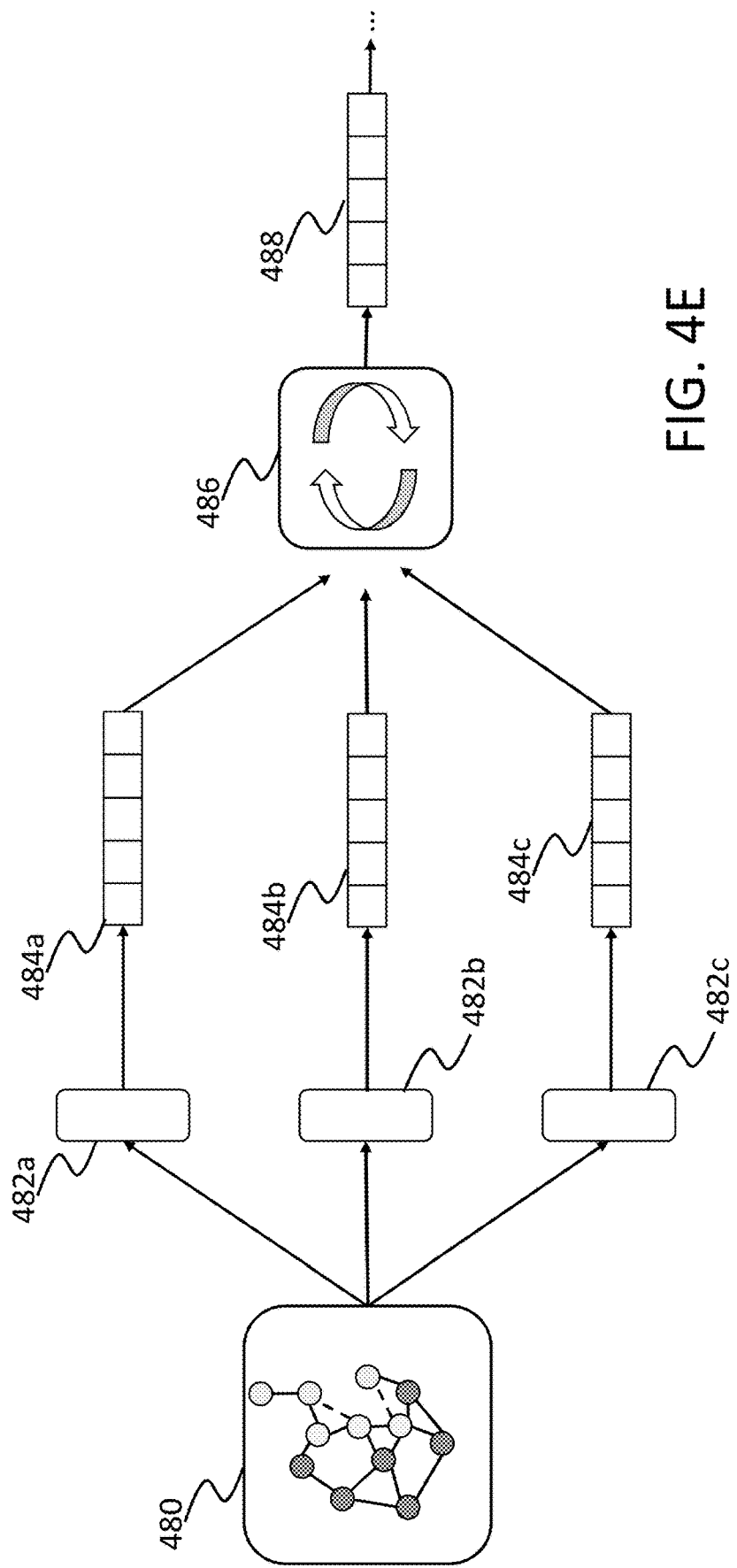

SYSTEMS AND METHODS FOR ARTIFICIAL INTELLIGENCE-BASED PREDICTION OF AMINO ACID SEQUENCES AT A BINDING INTERFACE

CROSS-REFERENCE TO RELATED APPLICATIONS

This application is a continuation-in-part of U.S. patent application Ser. No. 17/384,104, filed Jul. 23, 2021, entitled "Systems and Methods for Artificial Intelligence-Guided Biomolecule Design and Assessment". This application also claims priority to and benefit of: U.S. Provisional Patent Application No. 63/353,481, filed Jun. 17, 2022 and entitled "Systems and Methods for Artificial Intelligence-Based Prediction of Amino Acid Sequences at a Binding Interface;" and U.S. Provisional Patent Application No. 63/224,801, filed Jul. 22, 2021 and entitled "Systems and Methods for Artificial Intelligence-Guided Biomolecule Design and Assessment," the content of each of which is incorporated herein by reference in its entirety.

BACKGROUND

An increasing number of important drugs and vaccines are complex biomolecules referred to as biologics. For example, seven of the top ten best selling drugs as of early 2020 were biologics, including the monoclonal antibody adalimumab (Humira®). Biologics have much more complex structure than traditional small molecule drugs. The process of drug discovery, drug development, and clinical trials require an enormous amount of capital and time. Typically, new drug candidates undergo in vitro testing, in vivo testing, then clinical trials prior to approval.

Software tools for in silico design and testing of new drug candidates can cut the cost and time of the preclinical pipeline. However, biologics often have hard-to-predict properties and molecular behavior. To date, software and computational tools (including artificial intelligence (AI) and machine learning) have been applied primarily to small molecules, but, despite extensive algorithmic advances, have achieved little success in producing accurate predictions for biologics due to their complexity.

SUMMARY

Presented herein are systems and methods for prediction of protein interfaces for binding to target molecules. In certain embodiments, technologies described herein utilize graph-based neural networks to predict portions of protein/peptide structures that are located at an interface of custom biologic (e.g., a protein and/or peptide) that is being designed for binding to a target molecule, such as another protein or peptide. In certain embodiments, graph-based neural network models described herein may receive, as input, a representation (e.g., a graph representation) of a complex comprising a target and a partially-defined custom biologic. Portions of the partially-defined custom biologic may be known, while other portions, such an amino acid sequence and/or particular amino acid types at certain locations of an interface, are unknown and/or to be customized for binding to a particular target. A graph-based neural network model as described herein may then, based on the received input, generate predictions of likely acid sequences and/or types of particular amino acids at the unknown portions. These predictions can then be used to determine (e.g., fill in) amino acid sequences and/or structures to complete the custom biologic.

In one aspect, the invention is directed to a method for generating an amino acid interface of a custom biologic for binding to a target molecule in silico, the method comprising: (a) receiving (e.g., and/or accessing), by a processor of a computing device, a preliminary graph representation of a complex comprising (i) at least a portion of a target molecule and (ii) at least a portion of the custom biologic; (b) using, by the processor, the preliminary graph representation as input to a machine learning model (e.g., a graph neural network model) that generates, as output, a structural prediction for at least a portion of the complex (e.g., a graph representation comprising a probability distribution at each node) comprising (e.g., but not limited to) a prediction of an amino acid type and/or structure for each of one or more amino acid positions within an interface region of the custom biologic; and (c) using, by the processor, the interface prediction to determine the amino acid interface for the custom biologic.

In another aspect, the invention is directed to a system for generating an amino acid interface of a custom biologic, the system comprising a processor of a computing device and memory having instructions stored thereon, wherein the instructions, when executed by the processor, cause the processor to perform the method described above.

Features of embodiments described with respect to one aspect of the invention may be applied with respect to another aspect of the invention.

In one aspect, the invention is directed to a method for the in-silico design of an amino acid interface of a biologic for binding to a target (e.g., wherein the biologic is an in-progress custom biologic being designed for binding to an identified target), the method comprising: (a) receiving (e.g., and/or accessing), by a processor of a computing device, an initial scaffold-target complex graph comprising a graph representation of at least a portion of a biologic complex comprising the target and a peptide backbone of the in-progress custom biologic, the initial scaffold-target complex graph comprising: a target graph representing at least a portion of the target; and a scaffold graph representing at least a portion of the peptide backbone of the in-progress custom biologic, the scaffold graph comprising a plurality of scaffold nodes, a subset of which are unknown interface nodes, wherein each of said unknown interface nodes: (i) represents a particular (amino acid) interface site, along the peptide backbone of the in-progress custom biologic, that is [e.g., is a-priori known to be, or has been determined (e.g., by the processor) to be] located in proximity to one or more amino acids of the target, and (ii) has a corresponding node feature vector comprising a side chain type component vector (e.g., and/or side chain structure component vector) populated with one or more masking values, thereby representing an unknown, to-be determined, amino acid side chain [e.g., wherein the node feature vector further comprises (i) a constituent vector representing a local backbone geometry (e.g., representing three torsional angles of backbone atoms, e.g., using two elements for—a sine and a cosine of—each angle) and/or (ii) a constituent vector representing a side chain geometry (e.g., one or more chi angles)]; (b) generating, by the processor, using a machine learning model, one or more likelihood graphs based on the initial scaffold-target complex graph, each of the one or more likelihood graphs comprising a plurality of nodes, a subset of which are classified interface nodes, each of which: (i) corresponds to a particular unknown interface node of the scaffold graph and represents a same particular interface site along the peptide backbone of the in-progress custom biologic as the corresponding particular interface node, and (ii) has a corresponding node feature vector comprising a side chain component vector populated with one or more likelihood values (e.g., representing a likelihood that a side chain at the particular amino acid site is of a particular type); (c) using, by the processor, the one or more likelihood graphs to determine a predicted interface comprising, for each interface site, an identification of a particular amino acid side chain type; and, optionally, (d) providing (e.g., by the processor) the predicted interface for use in designing the amino acid interface of the in-progress custom biologic and/or using the predicted interface to design the amino acid interface of the in-progress custom biologic.

In certain embodiments, the target graph comprises a plurality of target nodes, each representing a particular (amino acid) site of the target and having a corresponding node feature vector comprising one or more constituent vectors (e.g., a plurality of concatenated constituent vectors), each constituent vector representing a particular (e.g., physical; e.g., structural) feature of the particular (amino acid) site. In certain embodiments, for each node feature vector of a target node, the one or more constituent vectors comprise one or more members selected from the group consisting of: a side chain type, representing a particular type of side chain (e.g., via a one-hot encoding scheme); a local backbone geometry [e.g., representing three torsional angles of backbone atoms (e.g., using two elements for—a sine and a cosine of—each angle)]; and a side chain geometry (e.g., one or more chi angles).

In certain embodiments, the target graph comprises a plurality of target edges, each associated with two particular target nodes and having a corresponding edge feature vector comprising one or more constituent vectors representing a relative position and/or orientation of two (amino acid) sites represented by the two particular target nodes.

In certain embodiments, the node feature vectors and/or edge feature vectors of the target graph are invariant with respect to three-dimensional translation and/or rotation of the target.

In certain embodiments, for each node feature vector of a target node, at least a subset of the one or more constituent vectors comprise absolute coordinate values (e.g., on a particular coordinate frame) of one or more atoms (e.g., backbone atoms; e.g., a beta carbon atom) of the particular amino acid site represented by the target node.

In certain embodiments, each of the plurality of scaffold nodes of the scaffold graph represents a particular (amino acid) site along the peptide backbone of the in-progress custom biologic and has a corresponding node feature vector comprising one or more constituent vectors, each constituent vector representing a particular (e.g., physical; e.g., structural) feature of the particular (amino acid) site. In certain embodiments, for each node feature vector of a scaffold node, the one or more constituent vectors comprise one or more members selected from the group consisting of: a side chain type, representing a particular type of side chain (e.g., via a one-hot encoding scheme); a local backbone geometry [e.g., representing three torsional angles of backbone atoms (e.g., using two elements for—a sine and a cosine of—each angle)]; and a side chain geometry (e.g., one or more chi angles).

In certain embodiments, the scaffold graph comprises a plurality of scaffold edges, each associated with two particular scaffold nodes and having a corresponding edge feature vector comprising one or more constituent vectors representing a relative position and/or orientation of two (amino acid) sites represented by the two particular scaffold nodes. In certain embodiments, the initial scaffold-target complex graph comprises a plurality of scaffold-target edges, each corresponding to (e.g., connecting) a particular scaffold node and a particular target node and having a corresponding edge feature vector comprising one or more constituent vectors representing a relative position and/or orientation of two (amino acid) sites represented by the particular scaffold node and the particular target node.

In certain embodiments, the node feature vectors and/or edge feature vectors of the scaffold graph are invariant with respect to three-dimensional translation and/or rotation of the peptide backbone of the in-progress custom biologic.

In certain embodiments, for each node feature vector of a target node, at least a subset of the one or more constituent vectors comprise absolute coordinate values (e.g., on a particular coordinate frame) of one or more atoms (e.g., backbone atoms; e.g., a beta carbon atom) of the particular amino acid site represented by the target node.

In certain embodiments, a subset of the scaffold nodes are known scaffold nodes, each having a node feature vector comprising a known side chain component representing a (e.g., a-priori known and/or previously determined) side chain type.

In certain embodiments, the machine learning model is or comprises a graph neural network.

In certain embodiments, step (b) comprises generating a plurality of likelihood graphs in an iterative fashion: in a first iteration, using the initial scaffold-target complex graph as an initial input to generate an initial likelihood graph; in a second, subsequent iteration, using the initial likelihood graph and/or an initial interface prediction based thereon, as input to the machine learning model, to generate a refined likelihood graph and/or a refined interface prediction based thereon; and repeatedly using the refined likelihood graph and/or refined interface prediction generated by the machine learning model at one iteration as input to the machine learning model for a subsequent iteration, thereby repeatedly refining the likelihood graph and or an interface prediction based thereon.

In another aspect, the invention is directed to a system for the in-silico design of an amino acid interface of a biologic for binding to a target (e.g., wherein the biologic is an in-progress custom biologic being designed for binding to an identified target), the system comprising: a processor of a computing device; and a memory having instructions stored thereon, wherein the instructions, when executed by the processor, cause the processor to: (a) receive (e.g., and/or access) an initial scaffold-target complex graph comprising a graph representation of at least a portion of a biologic complex comprising the target and a peptide backbone of the in-progress custom biologic, the initial scaffold-target complex graph comprising: a target graph representing at least a portion of the target; and a scaffold graph representing at least a portion of the peptide backbone of the in-progress custom biologic, the scaffold graph comprising a plurality of scaffold nodes, a subset of which are unknown interface nodes, wherein each of said unknown interface nodes: (i) represents a particular (amino acid) interface site, along the peptide backbone of the in-progress custom biologic, that is [e.g., is a-priori known to be, or has been determined (e.g., by the processor) to be] located in proximity to one or more amino acids of the target, and (ii) has a corresponding node feature vector comprising a side chain type component vector (e.g., and/or side chain structure component vector) populated with one or more masking values, thereby representing an unknown, to-be determined, amino acid side chain [e.g., wherein the node feature vector further comprises (i) a constituent vector representing a local backbone geometry (e.g., representing three torsional angles of backbone atoms, e.g., using two elements for—a sine and a cosine of—each angle) and/or (ii) a constituent vector representing a side chain geometry (e.g., one or more chi angles)]; (b) generate, using a machine learning model, one or more likelihood graphs based on the initial scaffold-target complex graph, each of the one or more likelihood graphs comprising a plurality of nodes, a subset of which are classified interface nodes, each of which: (i) corresponds to a particular unknown interface node of the scaffold graph and represents a same particular interface site along the peptide backbone of the in-progress custom biologic as the corresponding particular interface node, and (ii) has a corresponding node feature vector comprising a side chain component vector populated with one or more likelihood values (e.g., representing a likelihood that a side chain at the particular amino acid site is of a particular type); (c) use the one or more likelihood graphs to determine a predicted interface comprising, for each interface site, an identification of a particular amino acid side chain type; and, optionally, (d) provide the predicted interface for use in designing the amino acid interface of the in-progress custom biologic and/or using the predicted interface to design the amino acid interface of the in-progress custom biologic.

In certain embodiments, the target graph comprises a plurality of target nodes, each representing a particular (amino acid) site of the target and having a corresponding node feature vector comprising one or more constituent vectors (e.g., a plurality of concatenated constituent vectors), each constituent vector representing a particular (e.g., physical; e.g., structural) feature of the particular (amino acid) site. In certain embodiments, for each node feature vector of a target node, the one or more constituent vectors comprise one or more members selected from the group consisting of: a side chain type, representing a particular type of side chain (e.g., via a one-hot encoding scheme); a local backbone geometry [e.g., representing three torsional angles of backbone atoms (e.g., using two elements for—a sine and a cosine of—each angle)]; and a side chain geometry (e.g., one or more chi angles).

In certain embodiments, the target graph comprises a plurality of target edges, each associated with two particular target nodes and having a corresponding edge feature vector comprising one or more constituent vectors representing a relative position and/or orientation of two (amino acid) sites represented by the two particular target nodes.

In certain embodiments, the node feature vectors and/or edge feature vectors of the target graph are invariant with respect to three-dimensional translation and/or rotation of the target.

In certain embodiments, for each node feature vector of a target node, at least a subset of the one or more constituent vectors comprise an absolute (e.g., on a particular coordinate frame) of one or more atoms (e.g., backbone atoms; e.g., a beta carbon atom) of the particular amino acid site represented by the target node.

In certain embodiments, each of the plurality of scaffold nodes of the scaffold graph represents a particular (amino acid) site along the peptide backbone of the in-progress custom biologic and has a corresponding node feature vector comprising one or more constituent vectors, each constituent vector representing a particular (e.g., physical; e.g., structural) feature of the particular (amino acid) site. In certain embodiments, for each node feature vector of a scaffold node, the one or more constituent vectors comprise one or more members selected from the group consisting of: a side chain type, representing a particular type of side chain (e.g., via a one-hot encoding scheme); a local backbone geometry [e.g., representing three torsional angles of backbone atoms (e.g., using two elements for—a sine and a cosine of—each angle)]; and a side chain geometry (e.g., one or more chi angles).

In certain embodiments, the scaffold graph comprises a plurality of scaffold edges, each associated with two particular scaffold nodes and having a corresponding edge feature vector comprising one or more constituent vectors representing a relative position and/or orientation of two (amino acid) sites represented by the two particular scaffold nodes. In certain embodiments, the initial scaffold-target complex graph comprises a plurality of scaffold-target edges, each corresponding to (e.g., connecting) a particular scaffold node and a particular target node and having a corresponding edge feature vector comprising one or more constituent vectors representing a relative position and/or orientation of two (amino acid) sites represented by the particular scaffold node and the particular target node.

In certain embodiments, the node feature vectors and/or edge feature vectors of the scaffold graph are invariant with respect to three-dimensional translation and/or rotation of the peptide backbone of the in-progress custom biologic.

In certain embodiments, for each node feature vector of a target node, at least a subset of the one or more constituent vectors comprise absolute coordinate values (e.g., on a particular coordinate frame) of one or more atoms (e.g., backbone atoms; e.g., a beta carbon atom) of the particular amino acid site represented by the target node.

In certain embodiments, a subset of the scaffold nodes are known scaffold nodes, each having a node feature vector comprising a known side chain component representing a (e.g., a-priori known and/or previously determined) side chain type.

In certain embodiments, the machine learning model is or comprises a graph neural network.

In certain embodiments, the instructions, when executed by the processor, cause the processor to, in step (b), generate a plurality of likelihood graphs in an iterative fashion: in a first iteration, use the initial scaffold-target complex graph as an initial input to generate an initial likelihood graph; in a second, subsequent iteration, use the initial likelihood graph and/or an initial interface prediction based thereon, as input to the machine learning model, to generate a refined likelihood graph and/or a refined interface prediction based thereon; and repeatedly use the refined likelihood graph and/or refined interface prediction generated by the machine learning model at one iteration as input to the machine learning model for a subsequent iteration, thereby repeatedly refining the likelihood graph and or an interface prediction based thereon.

In another aspect, the invention is directed to a method for the in-silico design of an amino acid interface of a biologic for binding to a target (e.g., wherein the biologic is an in-progress custom biologic being designed for binding to an identified target), the method comprising: (a) receiving (e.g., and/or accessing), by a processor of a computing device, an initial scaffold-target complex graph comprising a graph representation (e.g., comprising nodes and edges) of at least a portion of a biologic complex comprising the target and a peptide backbone of the in-progress custom biologic; (b) generating, by the processor, using a machine learning model, a predicted interface comprising, for each of a plurality of interface sites, an identification of a particular amino acid side chain type; and (c) providing (e.g., by the processor) the predicted interface for use in designing the amino acid interface of the in-progress custom biologic and/or using the predicted interface to design the amino acid interface of the in-progress custom biologic.

In another aspect, the invention is directed to a system for the in-silico design of an amino acid interface of a biologic for binding to a target (e.g., wherein the biologic is an in-progress custom biologic being designed for binding to an identified target), the system comprising: a processor of a computing device; and a memory having instructions stored thereon, wherein the instructions, when executed by the processor, cause the processor to: (a) receive (e.g., and/or access) an initial scaffold-target complex graph comprising a graph representation (e.g., comprising nodes and edges) of at least a portion of a biologic complex comprising the target and a peptide backbone of the in-progress custom biologic; (b) generate, using a machine learning model, a predicted interface comprising, for each of a plurality of interface sites, an identification of a particular amino acid side chain type; and (c) provide the predicted interface for use in designing the amino acid interface of the in-progress custom biologic and/or use the predicted interface to design the amino acid interface of the in-progress custom biologic.

BRIEF DESCRIPTION OF THE DRAWING

The foregoing and other objects, aspects, features, and advantages of the present disclosure will become more apparent and better understood by referring to the following description taken in conjunction with the accompanying drawings, in which:

FIG. 4E is a schematic of a multi-headed neural network architecture, according to an illustrative embodiment;

Figure 1:
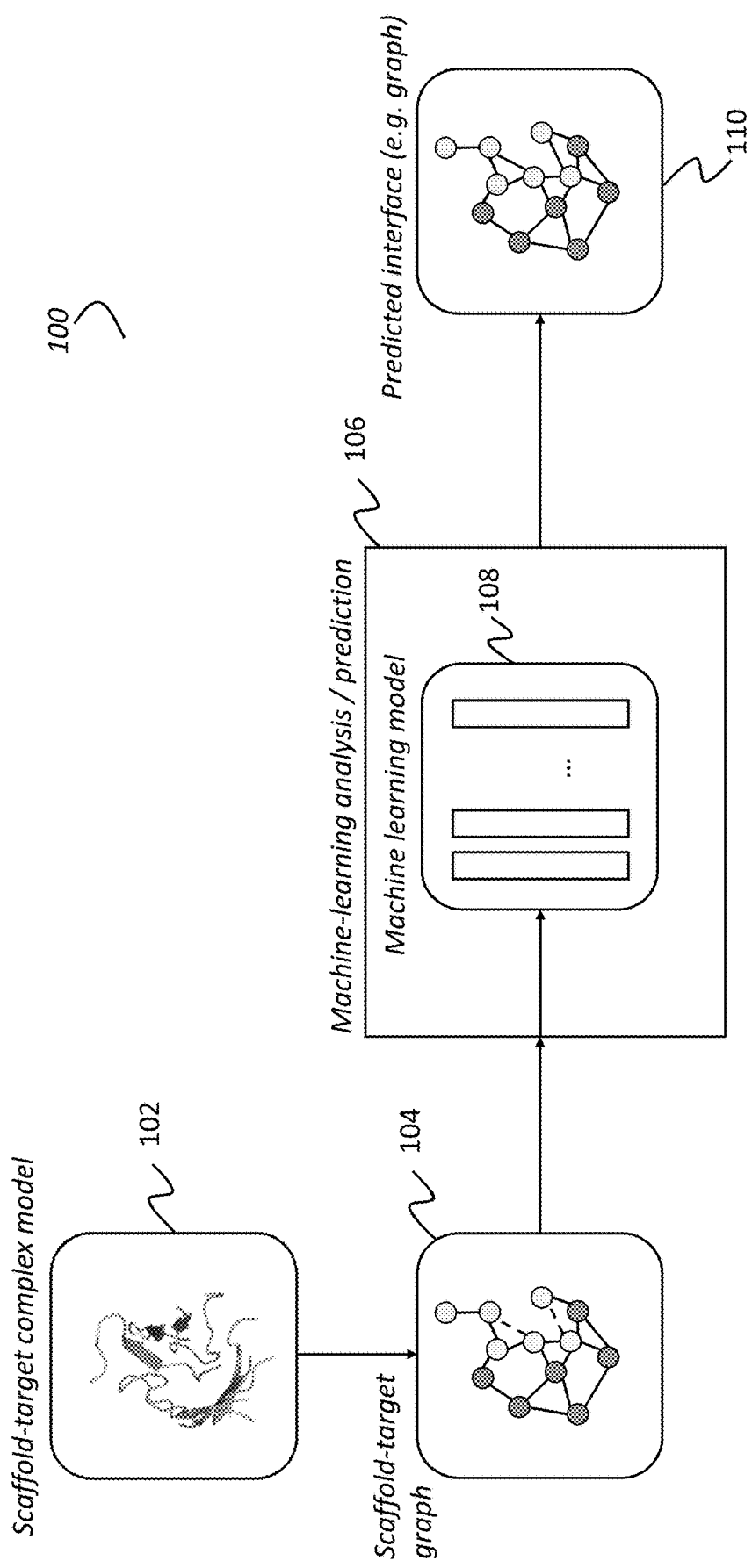
FIG. 1 is a block flow diagram of an example process for generating a predicted interface for use in design of a custom biologic, according to an illustrative embodiment.

Features and advantages of the present disclosure will become more apparent from the detailed description of certain embodiments that is set forth below, particularly when taken in conjunction with the figures, in which like reference characters identify corresponding elements throughout. In the figures, like reference numbers generally indicate identical, functionally similar, and/or structurally similar elements.

Certain Definitions

In order for the present disclosure to be more readily understood, certain terms are first defined below. Additional definitions for the following terms and other terms are set forth throughout the specification.

Comprising: A device, composition, system, or method described herein as "comprising" one or more named elements or steps is open-ended, meaning that the named elements or steps are essential, but other elements or steps may be added within the scope of the composition or method. To avoid prolixity, it is also understood that any device, composition, or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any device, composition, or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

A, an: As used herein, "a" or "an" with reference to a claim feature means "one or more," or "at least one."

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the tightness with which two or more binding partners associate with one another. Those skilled in the art are aware of a variety of assays that can be used to assess affinity, and will furthermore be aware of appropriate controls for such assays. In some embodiments, affinity is assessed in a quantitative assay. In some embodiments, affinity is assessed over a plurality of concentrations (e.g., of one binding partner at a time). In some embodiments, affinity is assessed in the presence of one or more potential competitor entities (e.g., that might be present in a relevant—e.g., physiological—setting). In some embodiments, affinity is assessed relative to a reference (e.g., that has a known affinity above a particular threshold [a "positive control" reference] or that has a known affinity below a particular threshold [a "negative control" reference"]. In some embodiments, affinity may be assessed relative to a contemporaneous reference; in some embodiments, affinity may be assessed relative to a historical reference. Typically, when affinity is assessed relative to a reference, it is assessed under comparable conditions.

Amino acid: in its broadest sense, as used herein, refers to any compound and/or substance that can be incorporated into a polypeptide chain, e.g., through formation of one or more peptide bonds. In some embodiments, an amino acid has the general structure $H_2N—C(H)(R)—COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Antibody, Antibody polypeptide: As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain which is homologous or largely homologous to an immunoglobulin-binding domain. In particular embodiments, "antibody polypeptides" encompasses polypeptides having a binding domain that shows at least 99% identity with an immunoglobulin binding domain. In some embodiments, "antibody polypeptide" is any protein having a binding domain that shows at least 70%, 80%, 85%, 90%, or 95% identity with an immuglobulin binding domain, for example a reference immunoglobulin binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In certain embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In certain embodiments, the "antibody polypeptide" is an antibody fragment that retains at least a significant portion of the full-length antibody's specific binding ability. Examples of antibody fragments include, but are not limited to, Fab, Fab', F(ab')2, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, the antibody polypeptides may be a humanized. Humanized antibody polypeptides include may be chimeric immunoglobulins, immunoglobulin chains or antibody polypeptides (such as Fv, Fab, Fab', F(ab')2 or other antigen-binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Backbone, peptide backbone: As used herein, the term "backbone," for example, as in a backbone or a peptide or polypeptide, refers to the portion of the peptide or polypeptide chain that comprises the links between amino acid of the chain but excludes side chains. In other words, a backbone refers to the part of a peptide or polypeptide that would remain if side chains were removed. In certain embodiments, the backbone is a chain comprising a carboxyl group of one amino acid bound via a peptide bond to an amino group of a next amino acid, and so on. Backbone may also be referred to as "peptide backbone". It should be understood that, where the term "peptide backbone" is used, it is used for clarity, and is not intended to limit a length of a particular backbone. That is, the term "peptide backbone" may be used to describe a peptide backbone of a peptide and/or a protein.

Biologic: As used herein, the term "biologic" refers to a composition that is or may be produced by recombinant DNA technologies, peptide synthesis, or purified from natural sources and that has a desired biological activity. A biologic can be, for example, a protein, peptide, glycoprotein, polysaccharide, a mixture of proteins or peptides, a mixture of glycoproteins, a mixture of polysaccharides, a mixture of one or more of a protein, peptide, glycoprotein or polysaccharide, or a derivatized form of any of the foregoing entities. Molecular weight of biologics can vary widely, from about 1000 Da for small peptides such as peptide hormones to one thousand kDa or more for complex polysaccharides, mucins, and other heavily glycosylated proteins. In certain embodiments, a biologic is a drug used for treatment of diseases and/or medical conditions. Examples of biologic drugs include, without limitation, native or engineered antibodies or antigen binding fragments thereof, and antibody-drug conjugates, which comprise an antibody or antigen binding fragments thereof conjugated directly or indirectly (e.g., via a linker) to a drug of interest, such as a cytotoxic drug or toxin. In certain embodiments, a biologic is a diagnostic, used to diagnose diseases and/or medical conditions. For example, allergen patch tests utilize biologics (e.g., biologics manufactured from natural substances) that are known to cause contact dermatitis. Diagnostic biologics may also include medical imaging agents, such as proteins that are labelled with agents that provide a detectable signal that facilitates imaging such as fluorescent markers, dyes, radionuclides, and the like.

In vitro: The term "in vitro" as used herein refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Native, wild-type (WT): As used herein, the terms "native" and "wild-type" are used interchangeably to refer to biological structures and/or computer representations thereof that have been identified and demonstrated to exist in the physical, real world (e.g., as opposed to in computer abstractions). The terms, native and wild-type may refer to structures including naturally occurring biological structures, but do not necessarily require that a particular structure be naturally occurring. For example, the terms native and wild-type may also refer to structures including engineered structures that are man-made, and do not occur in nature, but have nonetheless been created and (e.g., experimentally) demonstrated to exist. In certain embodiments, the terms native and wild-type refer to structures that have been characterized experimentally, and for which an experimental determination of molecular structure (e.g., via x-ray crystallography) has been made.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Peptide: The term "peptide" as used herein refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Polypeptide: As used herein refers to a polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Target: As used herein, the terms "target," and "receptor" are used interchangeably and refer to one or more molecules or portions thereof to which a binding agent—e.g., a custom biologic, such as a protein or peptide, to be designed—binds. In certain embodiments, the target is or comprises a protein and/or peptide. In certain embodiments, the target is a molecule, such as an individual protein or peptide (e.g., a protein or peptide monomer), or portion thereof. In certain embodiments, the target is a complex, such as a complex of two or more proteins or peptides, for example, a macromolecular complex formed by two or more protein or peptide monomers. For example, a target may be a protein or peptide dimer, trimer, tetramer, etc. or other oligomeric complex. In certain embodiments, the target is a drug target, e.g., a molecule in the body, usually a protein, that is intrinsically associated with a particular disease process and that could be addressed by a drug to produce a desired therapeutic effect. In certain embodiments, a custom biologic is engineered to bind to a particular target. While the structure of the target remains fixed, structural features of the custom biologic may be varied to allow it to bind (e.g., at high specificity) to the target.

Treat: As used herein, the term "treat" (also "treatment" or "treating") refers to any administration of a therapeutic agent (also "therapy") that partially or completely alleviates, ameliorates, eliminates, reverses, relieves, inhibits, delays onset of, reduces severity of, and/or reduces incidence of one or more symptoms, features, and/or causes of a particular disease, disorder, and/or condition. In some embodiments, such treatment may be of a patient who does not exhibit signs of the relevant disease, disorder and/or condition and/or of a patient who exhibits only early signs of the disease, disorder, and/or condition. Alternatively, or additionally, such treatment may be of a patient who exhibits one or more established signs of the relevant disease, disorder and/or condition. In some embodiments, treatment may be of a patient who has been diagnosed as suffering from the relevant disease, disorder, and/or condition. In some embodiments, treatment may be of a patient known to have one or more susceptibility factors that are statistically correlated with increased risk of development of a given disease, disorder, and/or condition. In some embodiments the patient may be a human.

Machine learning module, machine learning model: As used herein, the terms "machine learning module" and "machine learning model" are used interchangeably and refer to a computer implemented process (e.g., a software function) that implements one or more particular machine learning algorithms, such as an artificial neural networks (ANN), convolutional neural networks (CNNs), random forest, decision trees, support vector machines, and the like, in order to determine, for a given input, one or more output values. In some embodiments, machine learning modules implementing machine learning techniques are trained, for example using curated and/or manually annotated datasets. Such training may be used to determine various parameters of machine learning algorithms implemented by a machine learning module, such as weights associated with layers in neural networks. In some embodiments, once a machine learning module is trained, e.g., to accomplish a specific task such as determining scoring metrics as described herein, values of determined parameters are fixed and the (e.g., unchanging, static) machine learning module is used to process new data (e.g., different from the training data) and accomplish its trained task without further updates to its parameters (e.g., the machine learning module does not receive feedback and/or updates). In some embodiments, machine learning modules may receive feedback, e.g., based on user review of accuracy, and such feedback may be used as additional training data, for example to dynamically update the machine learning module. In some embodiments, a trained machine learning module is a classification algorithm with adjustable and/or fixed (e.g., locked) parameters, e.g., a random forest classifier. In some embodiments, two or more machine learning modules may be combined and implemented as a single module and/or a single software application. In some embodiments, two or more machine learning modules may also be implemented separately, e.g., as separate software applications. A machine learning module may be software and/or hardware. For example, a machine learning module may be implemented entirely as software, or certain functions of a ANN module may be carried out via specialized hardware (e.g., via an application specific integrated circuit (ASIC), field programmable gate arrays (FPGAs), and the like).

Substantially: As used herein, the term "substantially" refers to the qualitative condition of exhibiting total or near-total extent or degree of a characteristic or property of interest.

Scaffold Model: As used herein, the term "scaffold model" refers to a computer representation of at least a portion of a peptide backbone of a particular protein and/or peptide. In certain embodiments, a scaffold model represents a peptide backbone of a protein and/or peptide and omits detailed information about amino acid side chains. Such scaffold models, may, nevertheless, include various mechanisms for representing sites (e.g., locations along a peptide backbone) that may be occupied by prospective amino acid side chains. In certain embodiments, a particular scaffold models may represent such sites in a manner that allows determining regions in space that may be occupied by prospective amino acid side chains and/or approximate proximity to representations of other amino acids, sites, portions of the peptide backbone, and other molecules that may interact with (e.g., bind, so as to form a complex with) a biologic having the peptide backbone represented by the particular scaffold model. For example, in certain embodiments, a scaffold model may include a representation of a first side chain atom, such as a representation of a beta-carbon, which can be used to identify sites and/approximate locations of amino acid side chains. For example, a scaffold model can be populated with amino acid side chains (e.g., to create a ligand model that represents at least a portion of protein and/or peptide) by creating full representations of various amino acids about beta-carbon atoms of the scaffold model (e.g., the beta-carbon atoms acting as 'anchors' or 'placeholders' for amino acid side chains). In certain embodiments, locations of sites and/or approximate regions (e.g., volumes) that may be occupied by amino acid side chains may be identified and/or determined via other manners of representation for example based on locations of an alpha-carbons, hydrogen atoms, etc. In certain embodiments, scaffold models may be created from structural representations of existing proteins and/or peptides, for example by stripping amino acid side chains. In certain embodiments, scaffold models created in this manner may retain a first atom of stripped side chains, such as a beta-carbon atom, which is common to all side chains apart from Glycine. As described herein, retained beta-carbon atoms may be used, e.g., as a placeholder for identification of sites that can be occupied by amino acid side chains. In certain embodiments, where an initially existing side chain was Glycine, the first atom of glycine, which is hydrogen, can be used in place of a beta-carbon and/or, in certain embodiments, a beta carbon (e.g., though not naturally occurring in the full protein used to create a scaffold model) may be added to the representation (e.g., artificially). In certain embodiments, for example where hydrogen atoms are not included in a scaffold model, a site initially occupied by a Glycine may be identified based on an alpha-carbon. In certain embodiments, scaffold models may be computer generated (e.g., and not based on an existing protein and/or peptide). In certain embodiments, computer generate scaffold models may also include first side chain atoms, e.g., beta carbons, e.g., as placeholders of potential side chains to be added.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

Described herein are methods, systems, and architectures for designing interfaces of custom biologic structures for binding to particular targets of interest. In particular, as described in further detail herein, artificial-intelligence (AI)- based interface designer technologies of the present disclosure begin with a structural model of a particular target of interest and a partial, or incomplete, structural model of a custom biologic that is being/in the progress of being designed, for the purpose of binding to the target. The partial structural model of the in-progress custom biologic may include certain, for example, previously determined or known information about the custom biologic, but does not include an identification of a type (e.g., and/or a side chain geometry, e.g., one or more chi angles) of one or more amino acid side chains within an interface region that is expected to interact and influence binding with the target. That is, while structural features, such as a backbone geometry, of the in-progress custom biologic may be determined and/or known, an amino acid sequence within an interface region of the to-be designed custom biologic is as yet unknown, and to-be determined.

Interface designer technologies of the present disclosure utilize trained machine learning models in combination with a graph representation to generate, based on the structure of the particular target together with the partial model of the in-progress custom biologic, predicted interfaces—i.e., partial amino acid sequences within an interface region, that are determined, by the machine learning model, to bind (e.g., with high affinity) to a target.

FIG. 1 shows a schematic of an example overall approach 100 for generating predicted interfaces in accordance with the AI-based techniques described herein. For example, an interface design approach 100 in accordance with the present disclosure may use, as a starting point, a structural model of a complex 102 comprising at least a portion of a particular target and a portion of an in-progress custom biologic. In certain embodiments, a peptide backbone structure of the in-progress custom biologic is known and/or has been previously determined. As described herein, as well as, for example in U.S. patent application Ser. No. 17/384,104, entitled "Systems and Methods for Artificial Intelligence-Guided Biomolecule Design and Assessment," filed Jul. 23, 2021, incorporated herein by reference in its entirety, peptide backbone structures may be represented via scaffold models, which identify locations of backbone atoms, but leave amino acid side chains open/undefined. For example, at each of one or more amino acid sites, instead of including a representation of a particular side chain, a scaffold model may use a placeholder, such as a beta-carbon ($C_\beta$) atom. In certain embodiments, candidate peptide backbones for use in designing a custom biologic may be generated via machine learning techniques, such as a scaffold docker approach, described in further detain in U.S. patent application Ser. No. 17/384,104, entitled "Systems and Methods for Artificial Intelligence-Guided Biomolecule Design and Assessment," filed Jul. 23, 2021. A candidate peptide backbone may, accordingly, be used as a starting point or foundation, that can subsequently be populated with amino acids in an interface region to create a final custom biologic structure.

Accordingly, in certain embodiments, as shown in FIG. 1, an initial scaffold-target complex model 102, which includes a representation of the particular target along with a scaffold model representation of a candidate peptide backbone is received (e.g., from another computer module, such as a scaffold docker module) and/or accessed. As explained in further detail, interface designer technologies in certain embodiments described herein represent protein complexes as graphs, encoding structural features in vectors associated with nodes and edges. Accordingly, the initial scaffold-target complex model 102 may itself be, or used to generate, a scaffold-target graph 104, which is then used as input to a machine-learning step 106 that generates a predicted interface 110 (e.g., graph).

As described in further detail herein, machine learning step 106 utilizes a machine learning model 108 to perform a node classification operation that is used to generate the predicted interface 110. Predicted interface 110 may be a direct output of machine learning model 108, or, in certain embodiments, additional processing (e.g., post processing steps) is used to create a final predicted interface 110 from the output of machine learning model 108. Additionally or alternatively, multiple iterations and feedback loops may be used within machine learning step 106.

By utilizing a graph representation in conjunction with a machine learning model that performs a node classification operation, interface designer technologies described herein are able to generate direct predictions of amino acid interface sequences that are likely to be successful in binding to a particular target. This approach, accordingly, does not use the machine learning model as a scoring function, to evaluate candidate interface designs, but instead directly predicts a single interface. Directly predicting interfaces in this manner simplifies the AI-based biologic design process, reduces computational load, and facilitates training of the machine learning model itself.

Without wishing to be bound to any particular theory, it is believed that this approach of directly predicting interfaces as described herein provides several benefits over searching and scoring approaches. First, rather than generate numerous "guesses" of possible structures, and evaluating them via a machine learning model-based scoring function, direct prediction approaches as described herein generate one (or a few, if used in an iterative procedure) predictions of amino acid sequences at an interface. There is no need to generate guesses or search a landscape, thereby avoiding any need to employ complex searching routines such as simulated annealing to ensure a global, rather than local, optimum is obtained. Second, in a related benefit, direct prediction approaches can reduce the number of runs of a machine learning algorithm, since no searching is required. Third, since the direct prediction approaches described herein do not score an overall structure, so as to distinguish between structures that are or are not physically viable, there is no need to create any artificial training data (e.g., representing structures that are not-physically viable). Instead, structures from databases, such as the protein data bank (PDB) are sufficient. Training data can be created by masking a portion of a known structure, and having the machine learning algorithm attempt to recreate the ground truth. Accordingly, by allowing for direct prediction of amino acid interfaces, approaches described herein facilitate design of custom biologic structures.

A. Graph-Based Representation of Protein/Peptide Structure

In certain embodiments, structures of proteins and/or peptides, or portions thereof, may be represented using graph representations. Biological complexes, for example comprising multiple proteins and/or peptides, as well as, in certain embodiments small molecules, may also be represented using graph representations. An entire complex may be represented via a graph representation, or, in certain embodiments, a graph representation may be used to represent structure of a particular portion, such as in a vicinity of an interface between two or more molecules (e.g., constituent proteins and/or peptides of the complex).

Figure 2B:
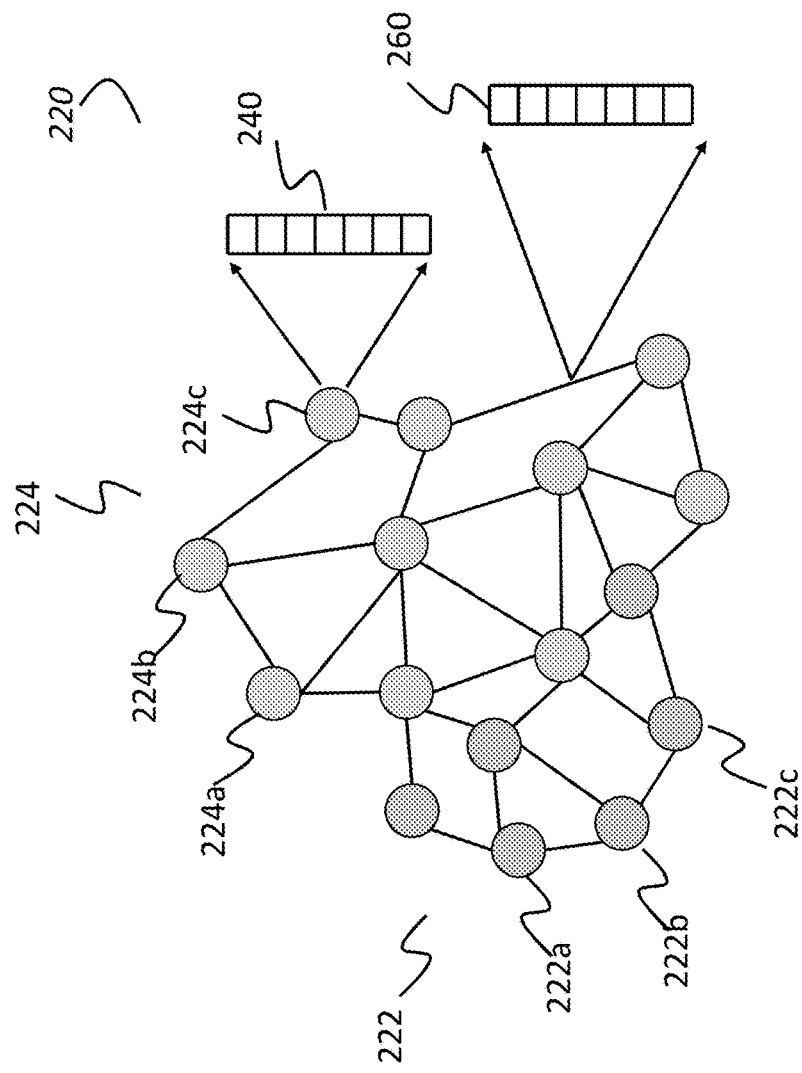
FIG. 2B is a diagram of a graph representation of a biologic complex, according to an illustrative embodiment.
Figure 2A:
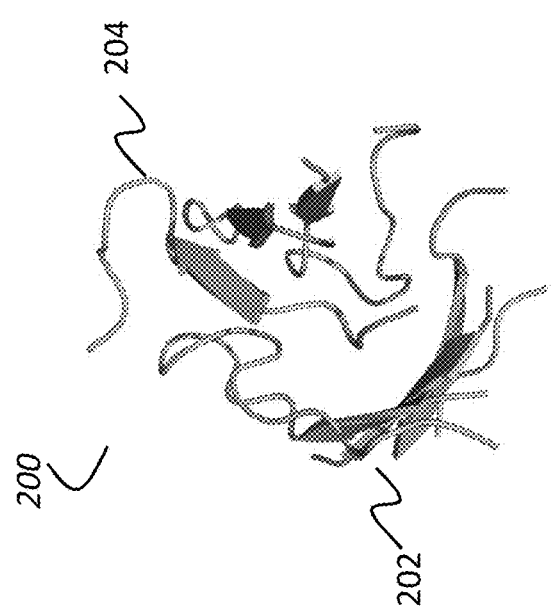
FIG. 2A is a ribbon diagram of a biologic complex, according to an illustrative embodiment.

For example, FIGS. 2A and 2B illustrate an approach for representing a portion of complex comprising a particular biologic (a protein or peptide) interacting with a target, which may be another protein or peptide, such as a particular receptor. FIG. 1A shows a ribbon diagram of the portion of the biological complex 200, comprising a portion of a particular biologic 204 (shown in green) together with a portion of the target 202 (shown in blue).

FIG. 2B shows a schematic of a graph representation 220 of the biological complex shown in FIG. 2A. As shown in FIG. 2B, in certain embodiments, the target and particular biologic may each be represented as a graph—a target graph 222 and a custom biologic graph 224. Each of graphs 222 and 224 comprise a plurality of nodes and, in certain embodiments, edges. In FIG. 2B, each node is illustrated as a circle and each edge is shown as a line connecting two nodes. The target graph is shown in blue, with nodes 222a, 222b, 222c and the biologic graph 224 is shown in green, with nodes 224a, 224b, 224c.

In certain embodiments, each node in a graph representation, such as target graph 222 and/or biologic graph 224, represents a particular amino acid site in the target or custom biologic and has a node feature vector 240 that is used to represent certain information about the particular amino acid site. For example, a node feature vector may represent information such as an amino acid side chain type, a local backbone geometry, a side chain rotamer structure, as well as other features such as a number of neighbors, an extent to which the particular amino acid site is buried or accessible, a local geometry, etc. Node feature vectors are described in further detail, for example, in section A.i below.

Edges in a graph representation may be used to represent interactions and/or relative positions between amino acids. Edges may be used to represent interactions and/or relative positioning between amino acids that are located within a same protein or peptide, as well as interactions between amino acids of different molecules, for example between the custom biologic and the target. As with nodes, each edge may have an edge feature vector 260. An edge feature vector may be used to represent certain information about an interaction and/or relative positioning between two amino acid sites, such as a distance, their relative orientation, etc. Edge feature vectors are described in further detail in section A.ii below.

In FIG. 2B, nodes representing amino acid sites of a (e.g., known) target molecule are shown in blue, and nodes representing amino acid sites of a custom biologic being designed are shown in green. Edges representing interactions within (i.e., between amino acids of) the target and the biologic are shown in blue and green, respectively. Edges representing an interaction and/or relative positioning between an amino acid of the target and one of the biologic—inter-chain edges—are shown in red.

A.i Node Features

Figure 3A:
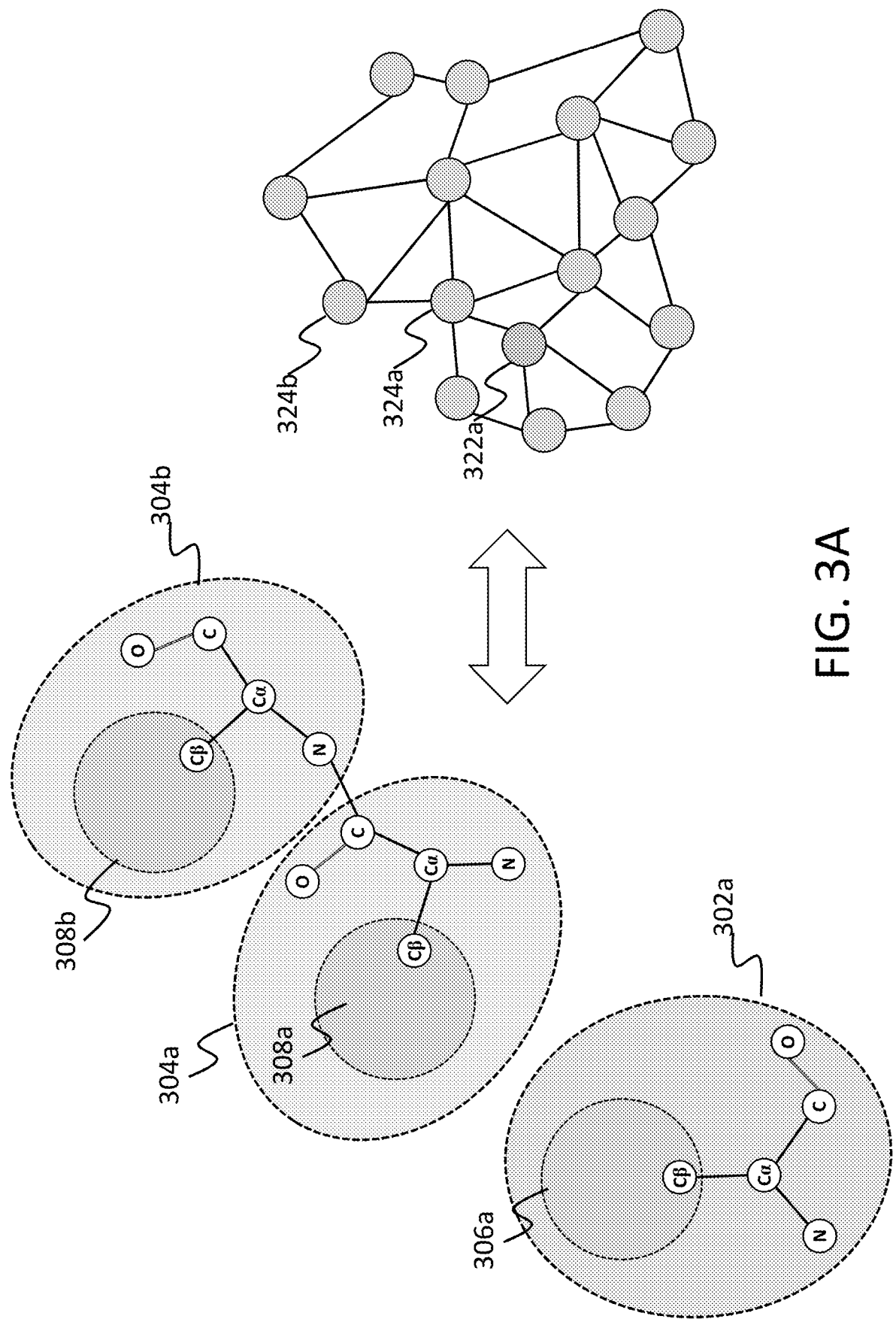
FIG. 3A is a diagram illustrating representation of amino acid sites of a biologic complex via nodes in a graph representation, according to an illustrative embodiment.

Turning to FIG. 3A, as described herein, nodes represent amino acid sites on a biologic and/or target, such as a protein or peptide. In certain embodiments, each amino acid site includes peptide backbone atoms (e.g., N, Cα, C, O, as shown in FIG. 3A) together with a side chain, which may be known, or as yet unknown, to-be-determined. For example, as shown in FIG. 3A, nodes 324a and 324b represent amino acid sites 304a and 304b of a particular custom biologic, each of which includes peptide backbone atoms along with a side chain, 308a and 308b, respectively. Side chains 308a and 308b may be unknown and/or to-be-determined, but can, for example, be approximately located by virtue of the beta-Carbon (Cβ) atoms as shown in FIG. 3A. Similarly, node 322a may be used to represent amino acid site 302a (which includes side chain 306a) of a target.

A node feature vector may be used to represent information about a particular amino acid site, such as side chain type (if known), local backbone geometry (e.g., torsional angles describing orientations of backbone atoms), rotamer information, as well as other features such as a number of neighbors, an extent to which the particular amino acid is buried or accessible, a local geometry, and the like. Various approaches for encoding such information may be used in accordance with technologies described herein.

Figure 3B:
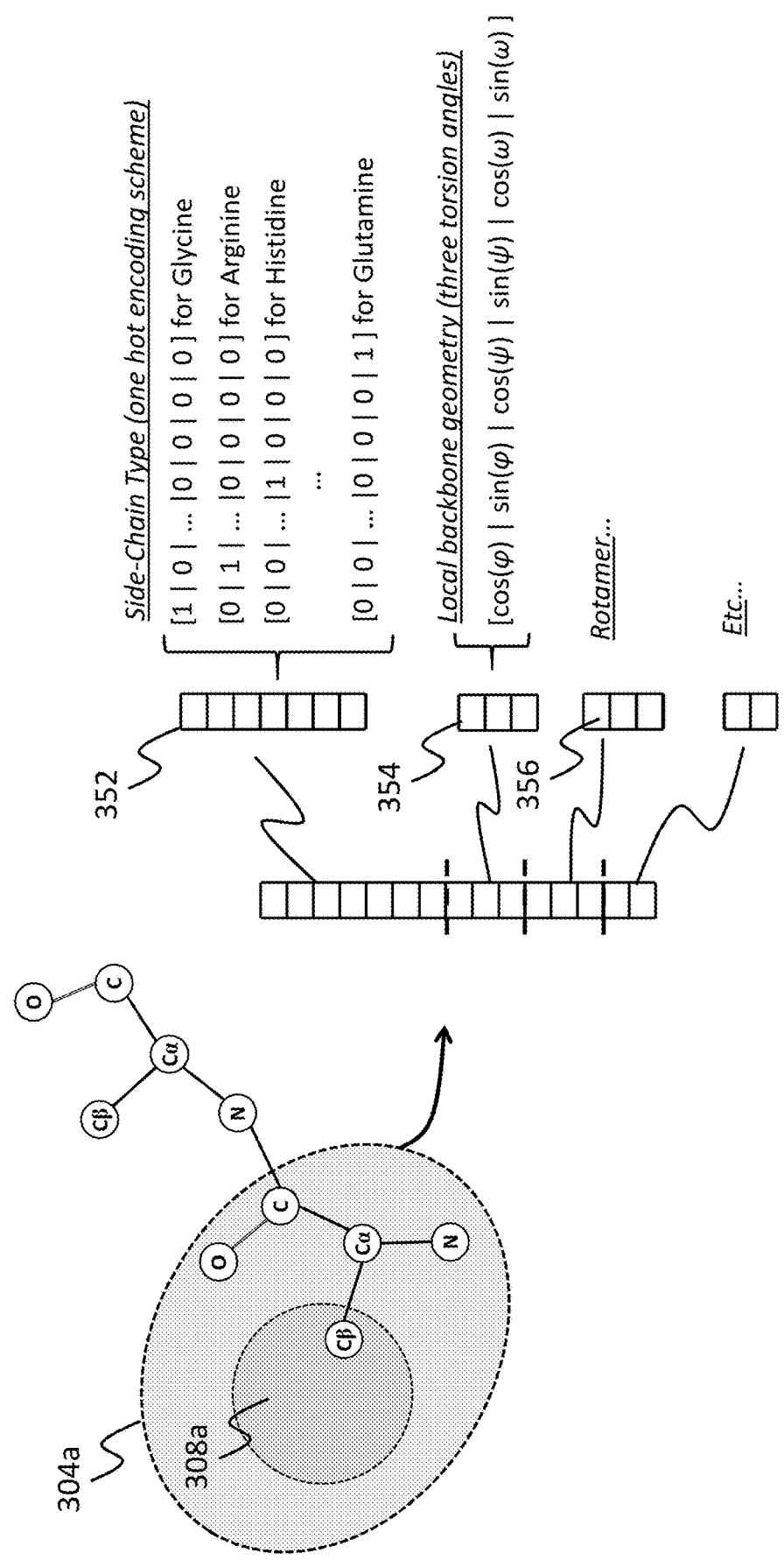
FIG. 3B is a diagram illustrating an example approach for encoding structural information of amino acid sites of a biologic via a node feature vector of a graph representation, according to an illustrative embodiment.

For example, in certain embodiments, a node feature vector comprises one or more component vectors, each component vector representing a particular structural feature at a particular amino acid location, as illustrated in FIG. 3B. That is, a node feature vector may be thought of as several component vectors 'stitched', or concatenated, together. Each component vector may include one or more elements, whose values encode a particular type of structural information. For example, as shown in FIG. 3B, one component vector 352 may be used to represent a type of side chain 308a, another component vector 354 used to encode local backbone geometry, another component vector 356 to encode rotamer structure of side chain 308a, and so on.

In certain embodiments, side chain type may be represented via a one-hot encoding technique, whereby each node feature vector comprises a twenty element side chain component vector 352 comprising 19 "0"s" and a single "1," with the position of the "1" representing the particular side chain type (e.g., glycine, arginine, histidine, lysine, serine, glutamine, etc.) at a particular node/amino acid site. In certain embodiments, local backbone geometry may be represented using three torsion angles (e.g., the phi ($\varphi$), psi ($\psi$), and omega ($\omega$) representation). In certain embodiments, a node feature vector may include a component vector representing a rotamer, for example a vector of chi angles. In certain embodiments, each angle may be represented by two numbers—e.g., a sine of the angle and a cosine of the angle.

A.ii Edges and Features

In certain embodiments, as described herein, edges may be used to represent interactions between and/or a relative positioning between two amino acid sites. A graph representation accounting for interactions between every amino acid could include, for each particular node representing a particular amino acid site, an edge between that node and every other node (e.g., creating a fully connected graph). In certain embodiments, a number of edges for each node may be limited (e.g., selected) using certain criteria such that each node need not be connected to every other node and/or only certain, significant, interactions are represented. For example, in certain embodiments, a k-nearest neighbor approach may be used, wherein interactions between a particular amino acid and its k nearest neighbors (k being an integer, e.g., 1, 2, 4, 8, 16, 32, etc.) are accounted for in a graph representation, such that each node is connected to k other nodes via k edges. In certain embodiments, a graph representation may only include edges for interactions between amino acids that are separated by a distance that is below a particular (e.g., predefined) threshold distance (e.g., 2 angstroms, 5 angstroms, 10 angstroms, etc.).

Figure 3C:
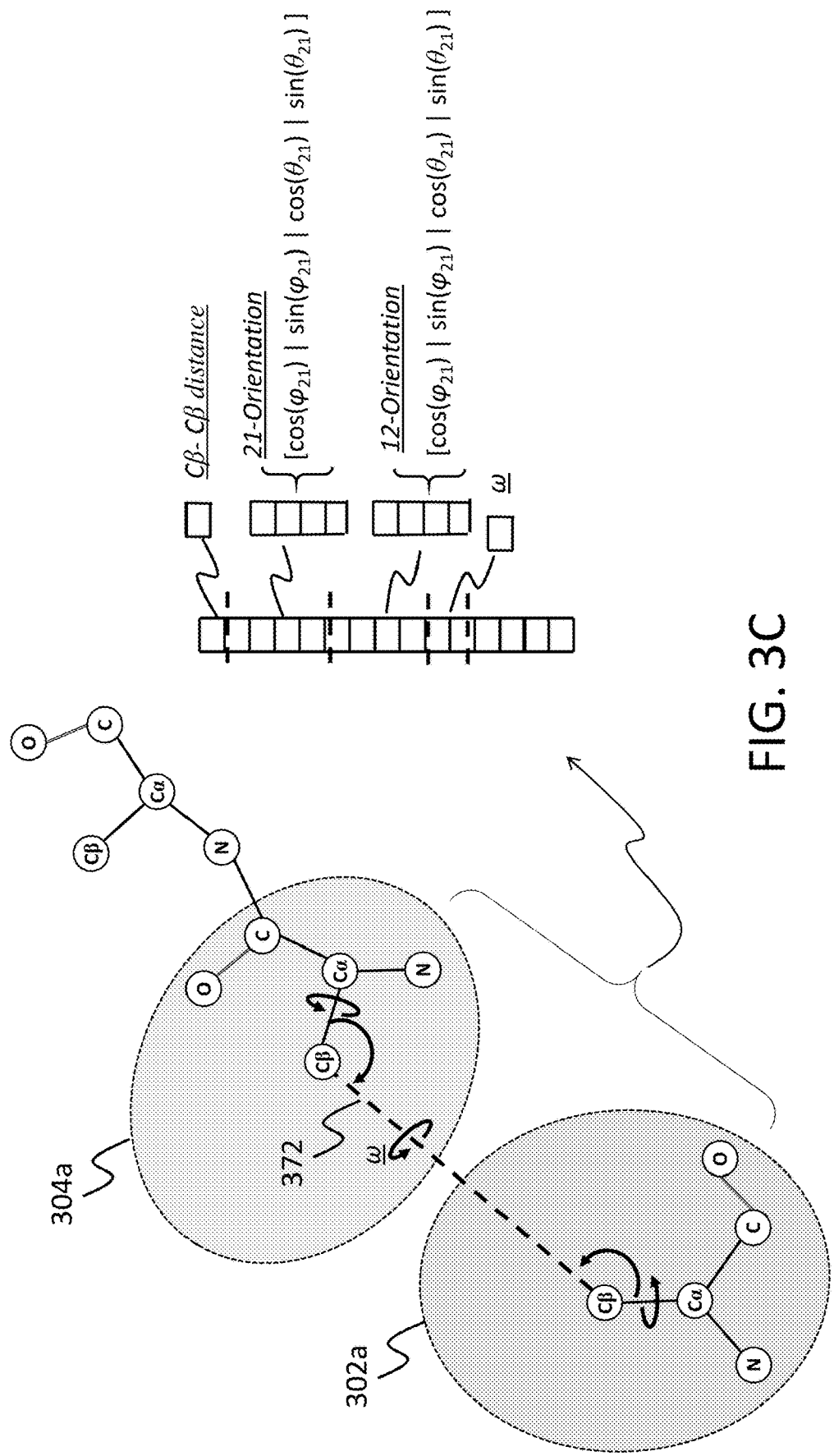
FIG. 3C is a diagram illustrating an example approach for encoding relational information (e.g., interactions and/or relative positioning between) two amino acid sites of a biologic via an edge feature vector of a graph representation, according to an illustrative embodiment.

Turning to FIG. 3C, in certain embodiments, an edge feature vector includes a representation of a relative distance and orientation between two amino acid sites. For example, an edge feature vector may include a value representing a distance 372 between beta-Carbon atoms of the two amino acid sites, along with values representing the three dihedral angles and two planar angles that represent their relative orientations. In certain embodiments, an edge feature vector may also include a value indicating whether the two nodes it connects represent amino acid sites on a same or different molecule.

A.iii Relative and Absolute Spatial Encoding Features

In certain embodiments, a graph representation may include only features that are invariant with respect to rotation and translation in three dimensional space. For example, as described above and illustrated in FIGS. 3A-C, local backbone torsion angles do not change when an entire biological complex is rotated and/or translated in 3D space. Likewise, edge feature vectors that represent relative distances between two amino acids, and their relative orientations with respect to each other also do not change when an entire biological complex is rotated and/or translated in 3D space. In certain embodiments, use of relative features, which are invariant under 3D translation/rotation is advantageous in that it obviates a need to train a machine learning model to avoid interpreting versions of a single structure that are rotated and/or translated as different structures.

Additionally or alternatively, in certain embodiments, absolute coordinate values, such as Cartesian x,y,z coordinates may be used in node feature vectors. In certain embodiments, this approach simplifies structural representations, for example allowing a graph to represent a 3D protein and/or peptide structure with only nodes and simplified edges (e.g., edges without information pertaining to relative position and/or orientation and/or distance between nodes, e.g., edges with a reduced number of features e.g., featureless edges). In certain embodiments, when absolute (as opposed to relative) coordinates are used, node features may no longer be invariant with respect to 3D rotation and/or translation and, accordingly, a training approach that ensures a machine learning model is equivariant to rotations and translations in 3D space is used.

B. Interface Prediction Using Graph Networks

Figure 4B:
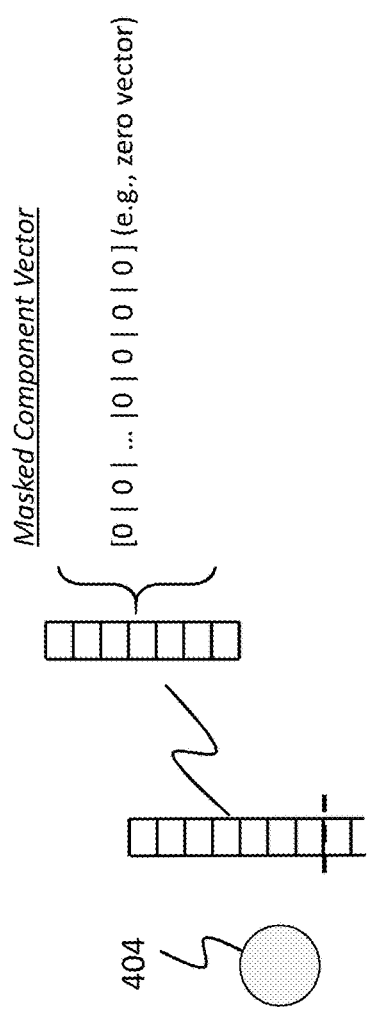
FIG. 4B is a diagram illustrating a masked component vector, according to an illustrative embodiment.
Figure 4A:
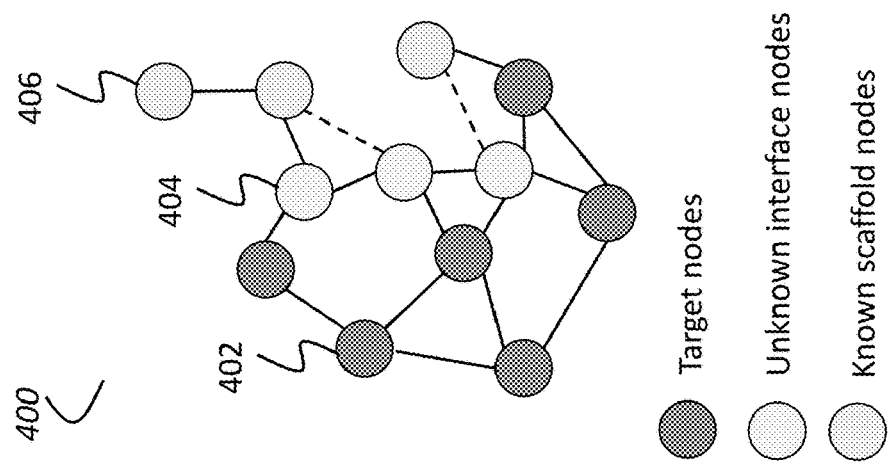
FIG. 4A is a diagram illustrating an initial complex graph comprising a target graph and a scaffold graph comprising unknown interface nodes and known scaffold nodes, according to an illustrative embodiment.
Figure 4C:
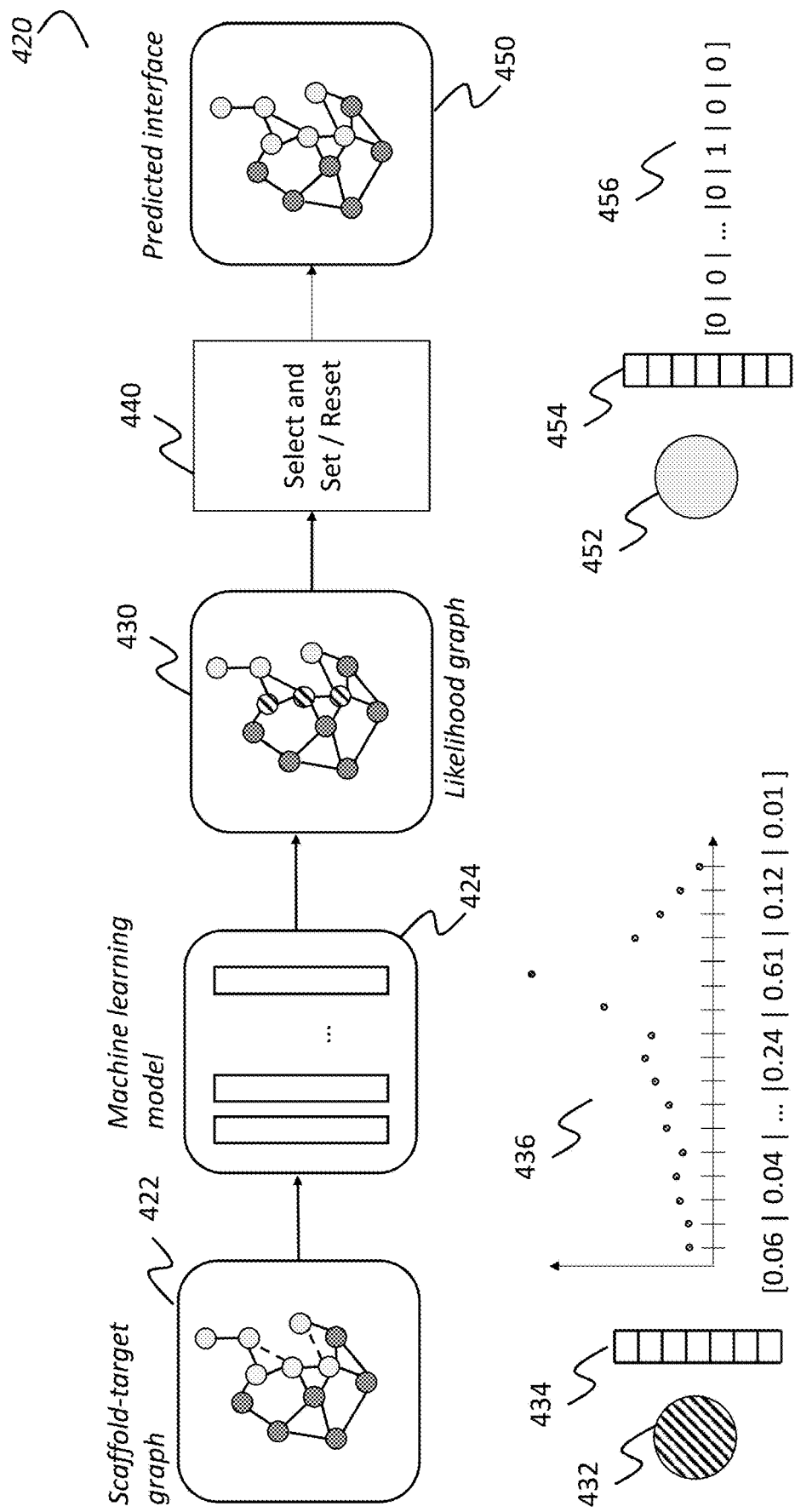
FIG. 4C is a block flow diagram of an example process for generating a predicted interface for use in design of a custom biologic, according to an illustrative embodiment.

Turning to FIGS. 4A-4C, graph representations of complexes comprising a partially unknown custom biologic may be used as input to a machine learning model (e.g., a graph neural network) in order to generate a predicted amino acid interface for binding to a particular target. In certain embodiments, a graph neural network is used to predict an amino acid interface by performing node classification and/or edge classification.

B.i Input Graph Representations and Component Masking

Turning to FIG. 4A, a graph neural network may receive a graph representation that comprises one or more unknown or partially unknown nodes and/or edges and be used to generate a prediction for the unknown nodes and/or edges. In certain embodiments, a portion of a biologic complex comprising a particular target together with an in-progress custom biologic that is being designed for binding to the target is represented via an initial complex graph 400.

In certain embodiments, the in-progress custom biologic is at a stage where its peptide backbone structure within and/or about its prospective binding interface has been designed and/or is known, but particular amino acid side chain types at interface sites, located in proximity to (e.g., one or more amino acids of) the target, are unknown, and to-be determined. For example, a scaffold model representing a prospective peptide backbone for the in-progress custom biologic may have been generated via an upstream process or software module, or accessed from a library of previously generated scaffold models. In certain embodiments, a scaffold docker module as described in U.S. patent application Ser. No. 17/384,104, filed Jul. 23, 2021, the content of which is hereby incorporated by reference in its entirety, may be used or may have been used to generate a scaffold model representing a prospective peptide backbone for the in-progress custom biologic.

Accordingly, initial complex graph 400 may include a target graph, representing at least a portion of the target, and a scaffold graph, representing at least a portion of the peptide backbone of the in-progress custom biologic. A scaffold graph may include a plurality of nodes, at least a portion of which are unknown interface nodes. Each unknown interface node (e.g., 404) represents a particular interface site along the peptide backbone of the in-progress custom biologic. Interface sites are amino acid sites that are either a-priori known or are/have been determined to be located in proximity to, and, accordingly, are expected to influence binding with, the target.

As illustrated in FIG. 4B, unknown interface nodes have node feature vectors with a side chain component vector that is masked so as to represent an unknown, to-be-determined amino acid side chain. Rather than being populated with a particular value or set of values that represents a particular type of amino acid side chain, a masked side chain component vector is populated with one or more masking values, that provide an indication that a particular side chain type is unknown or subject to change (e.g., by the machine learning model). A masked side chain component vector may be populated with one or more masking values. A variety of schemes with various combinations of masking values may be used to mask a side chain component vector. For example, in the context of the one-hot encoding scheme, describe herein with respect to FIG. 3B, as illustrated in FIG. 4B, a masked side chain component vector may be a zero vector. That is, while a particular side chain type can be represented by setting one element of a 20-length vector to "1", and the rest of the elements to "0", a masked side chain component can be represented via a 20-length zero vector. Additionally or alternatively, other values may be used, such as another integer (e.g., other than 1), or a null, or $\frac{1}{20}$ (e.g., indicating a uniform probability of each side chain type). In certain embodiments, a 21-element side chain component could be used, with the first 20 elements representing particular physical side chain types and the $21^{st}$ corresponding to an unknown side chain type.

In certain embodiments, node feature vectors of unknown interface nodes may also include components that represent information that is known, such as a local backbone geometry as described, e.g., in section A, herein. In certain embodiments, a scaffold graph may also include known scaffold nodes (e.g., 406) representing a portion of the in-progress custom biologic for which amino acid side chain types are known and/or desired to be fixed. A target graph may include a plurality of nodes (e.g., 402) each of which represents an amino acid site of the target and encodes structural information as described herein (e.g., in section A, above).

In certain embodiments, a scaffold graph may include edges. In certain embodiments, edges of a scaffold graph may all be known and/or fixed, or certain edges may be unknown and/or allowed to change. Such edges may have feature vectors that are completely or partially masked, using masking values in an analogous fashion to that described herein with respect to masked side chain components.

B.ii Machine Learning Model Output and Processing

FIG. 4C shows an example process 420 by which a machine learning model may be used to generate a predicted interface for an in-progress custom biologic using a graph representation approach as described herein. Machine learning model 424 may receive, as input, initial complex graph 422, comprising a target graph and scaffold graph.

Machine learning model 424 may include a plurality of layers and/or implement various architectures, examples of which are described in further detail herein. In certain embodiments, the machine learning model includes layers such as transformer layers, graph convolution layers, linear layers, and the like. In certain embodiments, the machine learning model is or includes a graph neural network that performs node and/or edge classification. In certain embodiments, a graph neural network may, for example, output a probability distribution for values of one or more unknown features of nodes and/or edges, which can then be evaluated to select a particular value for each unknown feature of interest.

For example, machine learning model 424 may receive initial complex graph 422 as input and generate, as output, a likelihood graph 430. Illustrative likelihood graph 430 comprises, for each unknown interface node of input scaffold graph portion of initial complex graph 422, a corresponding classified interface node 432 (shown with stripe fill). For a particular unknown interface node of the input scaffold graph, the corresponding classified interface node 432 has a node feature vector comprising a side chain component 434 that is populated with likelihood values 436. Likelihood values of classified interface node 434's node feature vector provide a measure of a predicted likelihood (e.g., of suitability for binding) for each particular side chain type, as determined by machine learning model 424. As illustrated in FIG. 4C, such likelihood values may, for example, be floating point number between zero and 1, thereby indicating a probability distribution for potential side chain types of classified interface node 434.

In certain embodiments, likelihood graph 430 may then be used to select 440, for each classified interface node, a determined side chain type, to create a predicted interface 450. For example, predicted interface 450 may be a graph, for which each node of the custom biologic is known—i.e., has a known side chain type. For example, values 456 of a side chain component vector 454 that represent a particular side chain type may be determined from likelihood values 436 by setting an element having a maximum likelihood to "1" and the rest to "0", thereby creating a known interface node 452 from a classified interface node 432. Likelihood values may be determined and used to create classified and known nodes in accordance with a variety of approaches and are not limited to the 0 to 1 probability distribution approach illustrated in FIG. 4C. For example, values ranging from 0 to 100, or on other scales may be used. Scales may be linear or non-linear. In certain embodiments, likelihood values may be output in a binary (e.g., 0 or 1) fashion, such that, for example, side chain components of classified nodes 432 are directly output in a one-hot encoding scheme and no selection step is needed to determine a final side chain component 456 from a classified node's likelihood values.

In certain embodiments, other information represented in components of node and/or edge feature vectors may be predicted in a likelihood graph by machine learning model 424. For example, likelihood values for rotamer structures of side chains, as well as orientations and/or distances encoded in edge feature vectors, may also be generated.

In certain embodiments, machine learning model 424 may generate predictions for node and/or edge features for an entire graph representation, e.g., including nodes/edges that are a priori known. That is, likelihood graph 430 may include classified interface nodes, as well as classified nodes that correspond to nodes of the input scaffold graph and/or target graph for which a side chain type was not masked, and previously known. In certain embodiments, to determine a final custom biologic interface, predictions for unknown/partially known nodes and/or edges are used to determine final feature values, while predictions for nodes and/or edges that are already known may be discarded, and a priori known values used. For example, selection step 440 may also reset side chain components of known scaffold nodes to their previously known values.

In certain embodiments, a neural network may be restricted to generate predictions for only a portion of a graph representation, for example, only for nodes (e.g., performing solely node classification), only for edges (e.g., performing solely edge classification), only for unknown features, or the like.

B.iii Single Run and Iteratively Refined Predictions

Figure 4D:
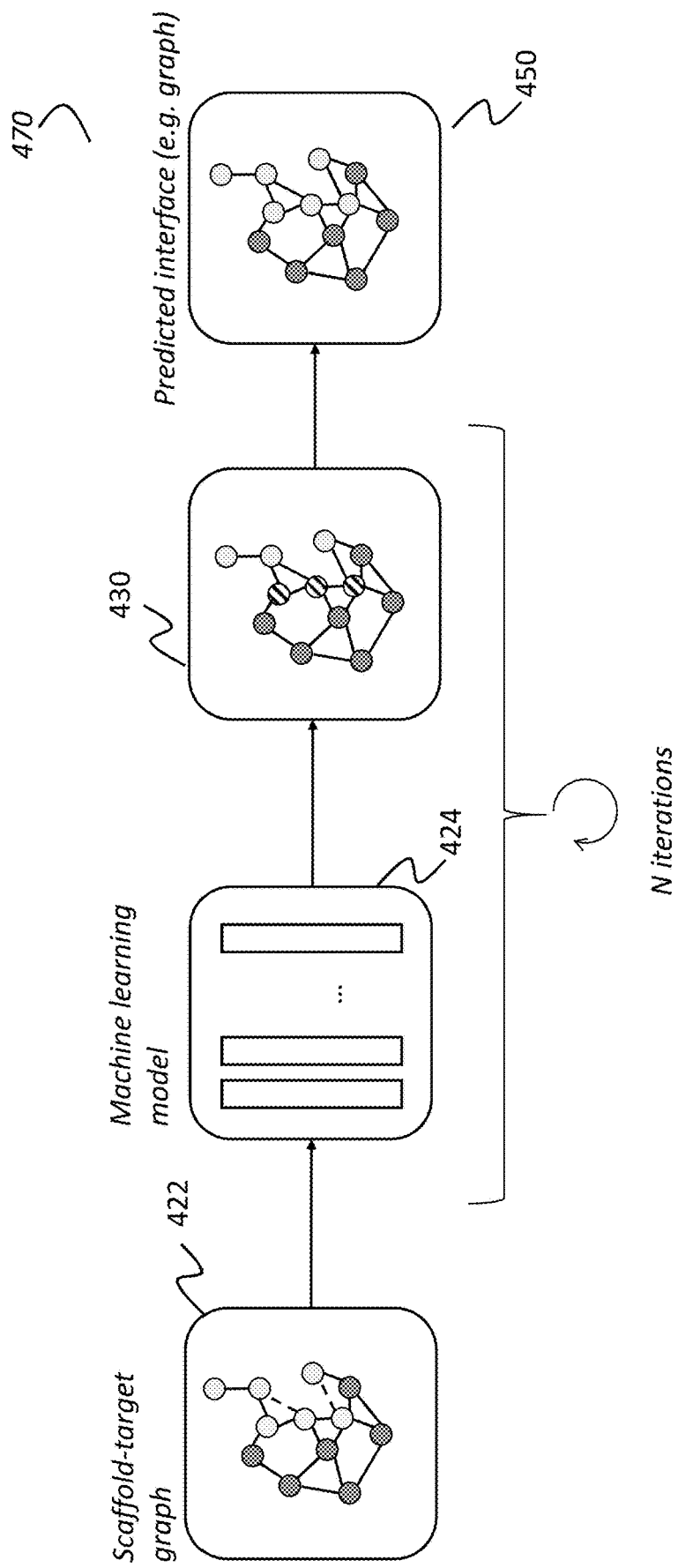
FIG. 4D is a block flow diagram of an example process for generating a predicted interface for use in design of a custom biologic, according to an illustrative embodiment.

Turning to FIG. 4D, in certain embodiments, as explained herein, a neural network may generate, as output, a structural prediction for an input graph representation. In certain embodiments, the structural prediction comprises, for each of one or more nodes and/or edges of the input graph representation, a prediction of one or more component features of an associated feature vector. For example, as explained herein, in the context of a prediction of a type of an amino acid, a neural network may generate a probability distribution comprising, for each possible type of amino acid, a likelihood that an amino acid represented by a particular node is of a particular type (e.g., glycine, arginine, histidine, lysine, serine, glutamine, etc.). In certain embodiments, such structural predictions may then be used to determine a final value of each component feature, for example, by identifying an amino acid type, for each node, predicted as having a maximum likelihood.

In certain embodiments, as shown in FIG. 4D, in an illustrative process 470, multiple iterations are performed, whereby a structural prediction generated from one iteration is fed back into the neural network as input for a subsequent iteration. Such structural predictions may be a likelihood graph 430, or intermediate predicted interfaces derived from a likelihood graph, via a selection and/or set/reset step 440 as described above.

That is, in certain embodiments, in an initial iteration, the machine learning model 424 receives, as input, initial complex graph 422 and generates as output initial likelihood graph 430. Then, initial likelihood graph itself is fed back into machine learning model 424, as input, to generate a refined likelihood graph. This process may be repeated in an iterative fashion, to successively refine likelihood graphs, with each iteration using a likelihood graph generated via a previous iteration as input. After the final iteration, predicted interface 450 is determined from a final likelihood graph.

In certain embodiments, at each iteration, rather than use a likelihood graph from a previous iteration as input, an intermediate predicted interface is generated and used as input. For example, in certain embodiments, in an initial iteration, machine learning model 424 receives, as input, initial complex graph 422 and generates as output initial likelihood graph 430. Initial likelihood graph 430 may then be used to generate an intermediate predicted interface, for example, by using classified nodes from likelihood graph to determine particular side chain types as described above with respect to FIG. 4C. The intermediate predicted interface may then be fed back into machine learning model 424, as input, to generate a refined likelihood graph, which, in turn, may be used to generate a refined predicted interface. This process may be repeated in an iterative fashion, to successively refine likelihood graphs and interface predictions, with each iteration using an interface prediction generated via a previous iteration as input. A final predicted interface 450 is produced on the final iteration.

Various numbers of iterations may be used. For example, two, five, ten twenty, fifty, 100, 250, 500, 1,000 or more iterations may be used. In certain embodiments, one or more thresholds are set to determine whether further iteration is necessary.

B.iv Neural Network Architectures

As shown in FIGS. 4C and 4D, a particular neural network model may comprise one or more (e.g., a plurality of) layers, including, for example, various transformer layers, graph convolutional layers, linear layers, etc. Each layer need not be of a same type, and various types of layers (e.g., transformer, graph convolutional, linear) may be combined in a particular neural network model.

Turning to FIG. 4E, in certain embodiments, a neural network model may be a multi-headed model that utilizes multiple 'input heads'—parallel sets of neurons within each of one or more particular layers—to separately process different classes of interactions between amino acids. As opposed to 'attention heads' which are sets of neurons (learnable parameters) that receive the same input and generate a corresponding output, these 'input heads' operate on different inputs with each head specialized for its own particular kind of input. For example, in certain embodiments, a three-headed network model may be used in which each of one or more layers of a neural network model comprises three parallel sets of neurons, each associated with a different type of interaction. In certain embodiments, other approaches comprising more or less than three 'input heads' may be used. For example, each input head may be specialized for a certain edge type (e.g., where each input head has neurons/weights that are specialized on a specific edge type), and they can be concatenated or otherwise combined.

In this way, multiple input heads are allocated to receive different 'versions' of the same graph. For example, each version could include a certain subset of the edges in the graph, for example, and omit other edges. For example, in certain embodiments, a first set of neurons may, for example, evaluate, for each node, $k_1$ edges and corresponding neighbor nodes that represent the $k_1$ nearest neighbor amino acids. A second set of neurons may then be associated with, and process, for each node, $k_2$ edges and corresponding neighbor nodes that represent the interactions between $k_2$ nearest neighboring amino acids. Finally, a third set of neurons may then be associated with, and process, for each node, $k_3$ edges and corresponding neighbor nodes that represent the interactions between $k_3$ nearest neighboring amino acids. $k_1$, $k_2$, and $k_3$ may be integers, with $k_1 < k_2 < k_3$, (e.g., $k_1=8$, $k_2=16$, and $k_3=32$) such that the first set of neurons tends to be associated with short range interactions, the second set of neurons tends to be associated with intermediate range interactions, and the third set of neurons tends to be associated with long range interactions.

Additionally or alternatively, in certain embodiments various sets of neurons in a multi-headed network may be associated with different types of interactions between amino acids based on other criteria. For example, three different sets of neurons may be associated with (i) peptide bond interactions, (ii) intra-chain interactions (e.g., interactions between amino acids within a same molecule) and (iii) inter-chain interactions (e.g., interactions between amino acids on different molecules), respectively. Thus, for example, where three input heads are used, one input head might only consider edges that represent peptide bonds, another input head only considers edges that represent intra-chain interactions, and another input head only considers edges that represent inter-chain interactions.

In certain examples, other ways of organizing/defining input heads are implemented according to what a particular input head is dedicated to. For example, there could be one or more input heads, each of which only considers edges that represent interactions between amino acid sites that are within a particular threshold distance of each other (e.g., a first input head for 5 angstroms or less, a second input head for 10 angstroms or less, and a third input head for 15 angstroms or less). In another example, there could be one or more input heads, each of which considers a first k (where k is an integer) edges that are the k nearest neighbors (e.g., a first input head that considers the 5 nearest neighbors, a second input head that considers the 15 nearest neighbors, and a third input head that considers the 30 nearest neighbors).

Furthermore, in an alternative embodiment, both inter and intra-chain interactions can be combined in one input head (receives both inter and intra chain edges), for example, with an additional value on the end of each edge feature vector that serves as a "chain label"—e.g., "1" if the edge is an inter-chain edge and "0" if the edge is an intra chain edge. Moreover, in certain embodiments, redundant information could be eliminated, thereby simplifying the task for the neural network. For example, backbone torsion angles have some redundancy according to the edge definitions—certain edges may be simplified by removing degrees of freedom, and certain angles may be computed using information about the orientation of neighboring amino acids.

The sets of edges considered by different input heads may be overlapping or non-overlapping sets. For example, a set of intra-chain edges and a set of inter-chain edges are generally non-overlapping, while a set of edges representing sites within 5 angstroms or less and a set of edges representing sites within 10 angstroms or less are overlapping (the second set includes the first). In certain embodiments, various input heads may be used in different combinations in a single machine learning model.

In certain embodiments, an ensemble machine learning model is created as a collection of multiple subsidiary machine learning models, where each subsidiary machine learning model receives input and creates output, then the outputs are combined (e.g., a voting model). For example, in certain embodiments, a voting ensemble machine learning model may be used wherein a likelihood value is an integer, such as a sum of votes of multiple machine learning models. For example, as applied in the method illustrated in FIG. 4C, the values 436 of predicted likelihood (e.g., of suitability for binding) for each particular side chain type, as determined by machine learning model 424, may be integers representing sums of votes of multiple machine learning models in a voting ensemble machine learning model, thereby indicating a probability distribution for potential side chain types of the classified interface node 434 in the example. Certain embodiments use different ways of combining subsidiary machine learning model output in a voting model. For example, a simple average may be taken, a weighted average may be taken (e.g., where some models are weighted more heavily than others), votes may be counted (e.g., integers), and the like. Where subsidiary machine learning models are weighted, a weighting function may be used according not only to the model, but also according to the particular side chain. For instance, for a first model, predictions made of hydrophobic side chains may be weighted heavily, whereas, for a second model, predictions of hydrophilic side chains are weighted heavily.

In the schematic of FIG. 4E, three 'input heads' are depicted 482a, 482b, and 482c, where each input head receives and processes a portion of the edges of the scaffold-target graph 480 and generates output vectors 484a, 484b, and 484c, allowing the processing of different ranges or scales of information. For example, input head 482a may process inter-chain edges, input head 482b may process intra-chain edges, and input head 482c may process edges that represent peptide bonds, i.e., connecting neighboring amino acid sites. At step 486, the output may be concatenated, averaged, added, weighted, and/or otherwise processed to produce combined output vector 488.

Figure 4F:
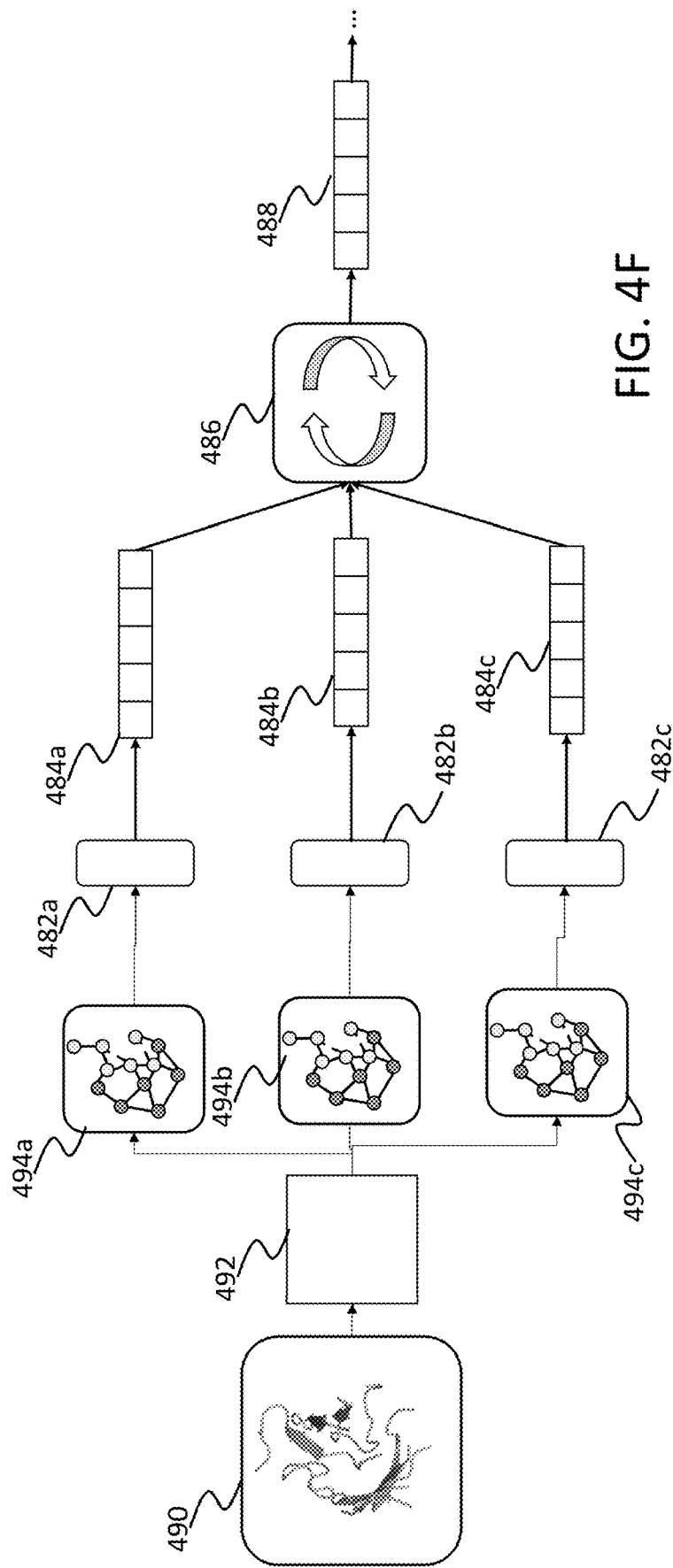
FIG. 4F is a schematic of a multi-headed neural network architecture with a graph featurizer module, according to an illustrative embodiment.

The schematic of FIG. 4F depicts how graph versions for input may be created from an initial graph (e.g., by selecting and retaining various sets of edges) or may be created directly from a structural model of the biologic complex 490. For example, as shown in FIG. 4F, a graph featurizer module 492 may operate on a biologic complex model 490 (e.g., a protein data bank (PDB) file) and generate multiple graph representations 494a, 494b, and 494c, each used as input to a corresponding input head 482a, 482b, and 482c. In certain embodiments, two or more of the generated graph representations may use the same edge feature vector scheme. In certain embodiments, two or more generated graphs may use a different approach for representing edge feature vectors, e.g., to encode different types of information. For example, graph 494a and 494b might both include edges that have feature vectors conveying the structural information as shown in FIG. 3C (except that one graph might include k=5 nearest neighbors and the other graph might include the k=10 nearest neighbors, for instance), while graph 494c may use a different scheme for encoding structure information in an edge feature vector (for instance, where edges are limited to peptide bonds, with each edge having a feature vector that has two elements indicating which amino acid is upstream from the other). At step 486, the output may be concatenated, averaged, added, weighted, and/or otherwise processed to produce combined output vector 488.

C. Example Training and Performance of a Side Chain Classification Network

This example shows a training procedure, and performance results for an example graph network approach for predicting side chain types in accordance with the embodiments described herein.

C.i Example Training Procedure

Figure 5A:
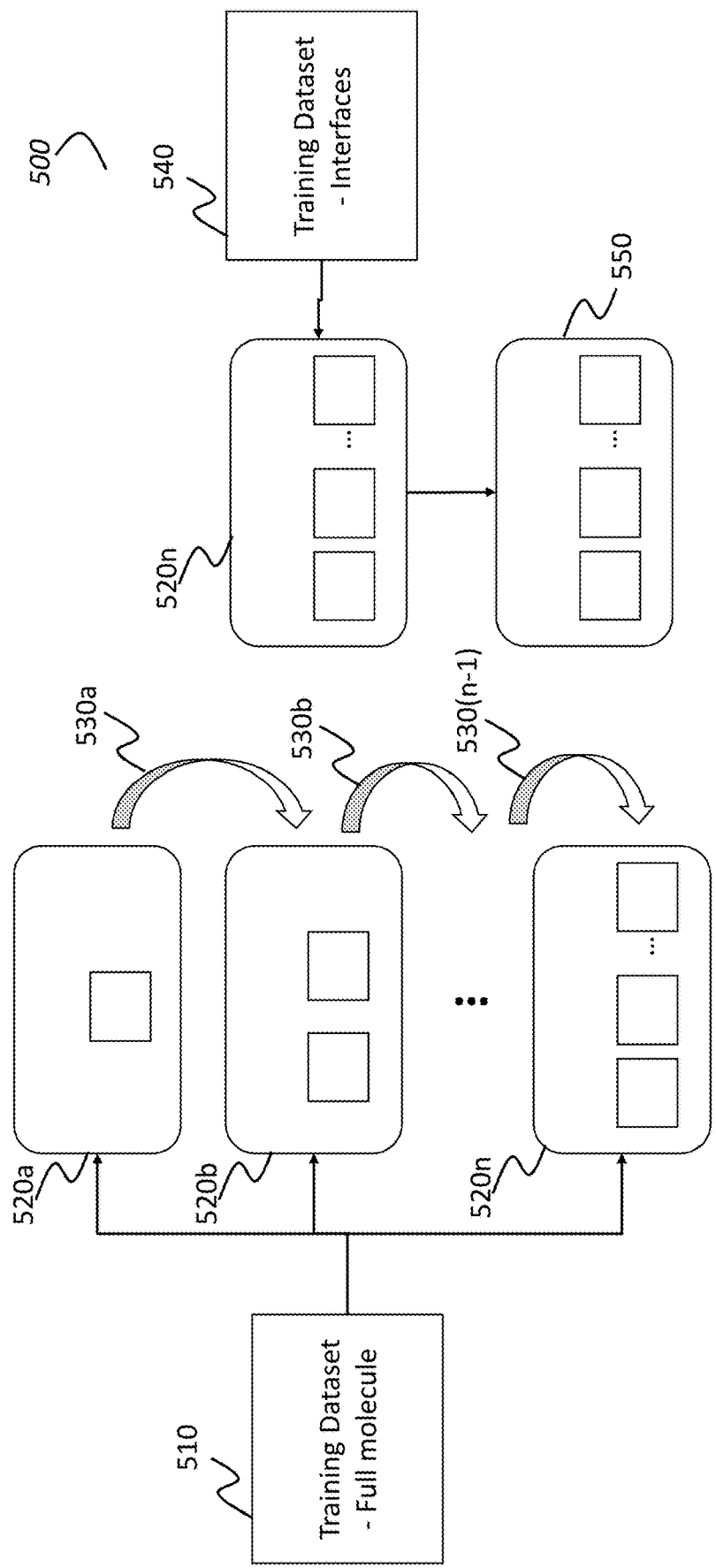
FIG. 5A is a block flow diagram showing an example training procedure for training a machine learning model to generate predicted interfaces for use in design of a custom biologic, according to an illustrative embodiment.
Figure 5B:
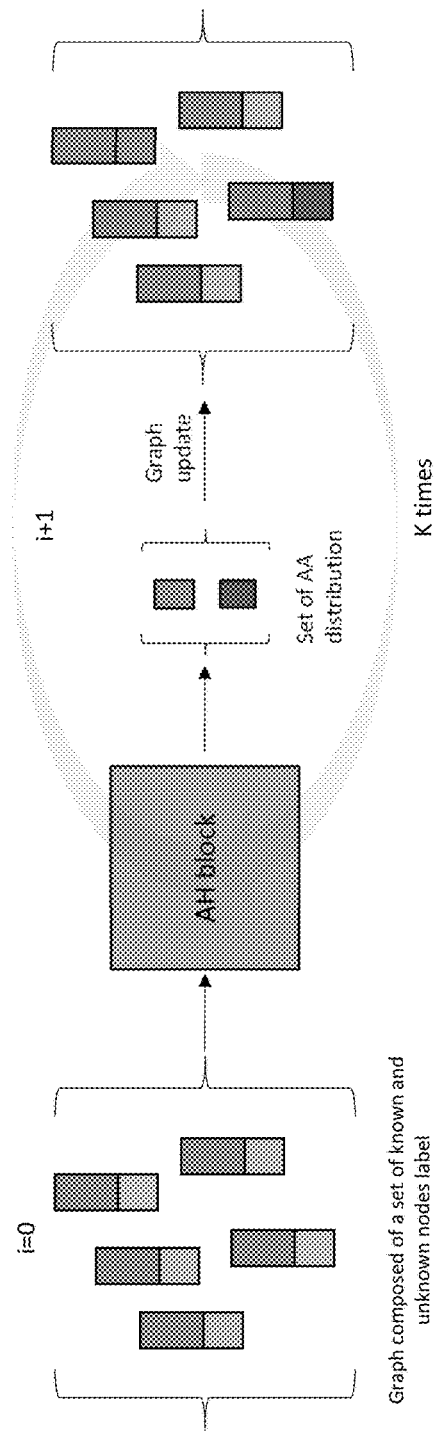
FIG. 5B is a diagram showing an example training procedure for training a machine learning model to generate predicted interfaces for use in design of a custom biologic, according to an illustrative embodiment.
Figure 5C:
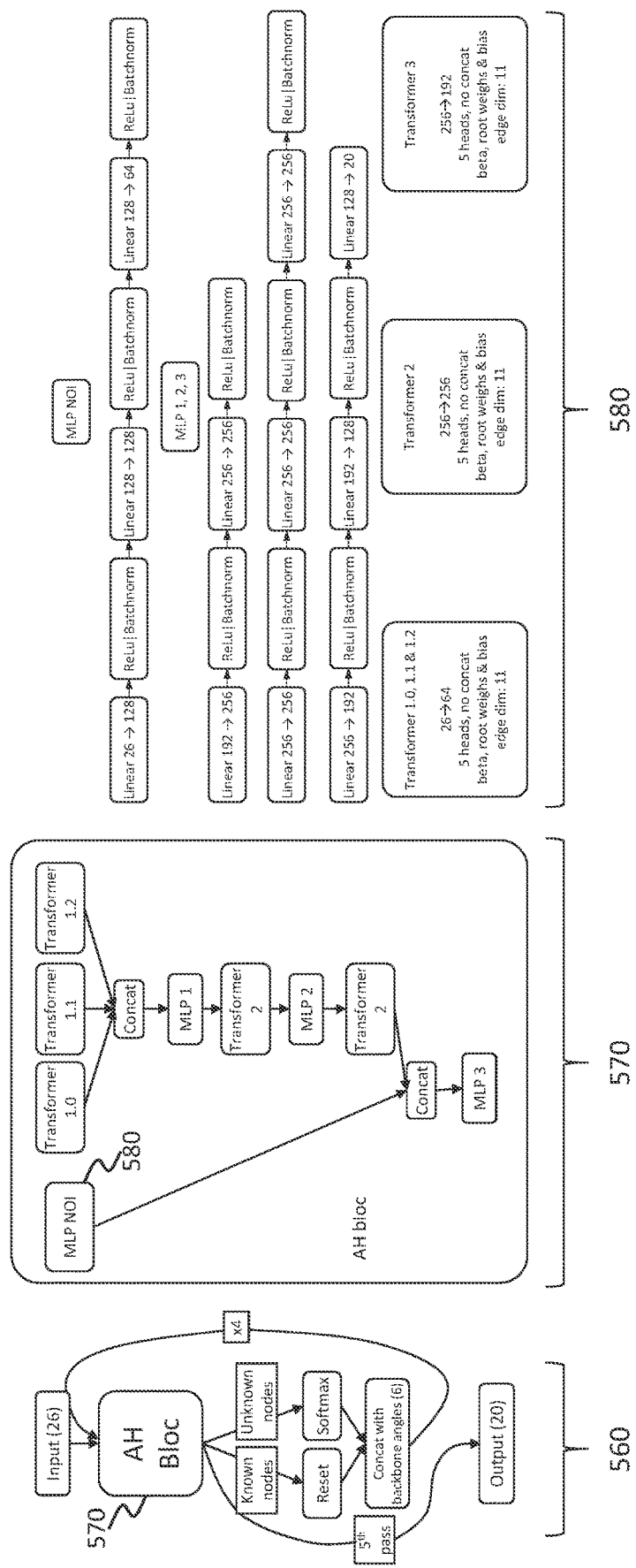
FIG. 5C is a schematic of a (e.g., stackable) block for use in a graph network approach, according to an illustrative embodiment.

FIGS. 5A-C illustrate an approach for training a graph-based neural network used in certain embodiments described herein. The particular network utilized in this example comprises multiple blocks, which may be combined together in a pipeline. FIG. 5A shows an outline of an illustrative process 500 for training a graph-based neural network comprising multiple blocks. In certain embodiments, a graph based neural network may be trained using data from structural models of proteins and/or peptides, for example obtained from the protein data bank (PDB). In certain embodiments, input graph representations are created from structural models, according to the approaches for representing amino acids and their interactions via nodes and edges as described herein. In certain embodiments, training data is created by masking various nodes and/or edges of a known structural model, leaving the masked portions for the neural network to predict during the training process.

For example, as shown in FIG. 5A, training data set 510 was created using graph representations created from structural models obtained from the PDB. Various training representations were created by randomly selecting portions of a molecule and/or complex to mask (e.g., such that a predefined amount, e.g., ⅓ of the molecule or complex, is masked). The particular amino acid sites that were masked were not restricted to a particular region, such as an interface, of a molecule or complex, but were allowed to vary randomly throughout the full molecule or complex. This "full molecule" training dataset 510 was then used for a first round of training, that used multiple steps to successively add blocks to and train a multi-block machine learning model. As shown in FIG. 5A, in a first step, full molecule training dataset 510 was used to train a single block model 520a, generating a first set of layer weights for the single block. These layer weights were then used to initialize 530a a two block model 520b, which was then trained, again using training dataset 510, to determine a second set of layer weights. These second set of layer weights were used to initialize a three block model. This process was repeated, adding an additional block at each step, and initializing layer weights using weights from a preceding step, was repeated, out to n (a desired number of) iterations and size (i.e., number of blocks) in an $n^{th}$ model 520n. At each step, training was performed using a cross entropy loss function.

A variety of size models and iterations, for example, two, five, ten twenty, fifty, 100, 250, 500, 1,000 or more may be used. In certain embodiments, one or more thresholds are set to determine whether further iteration is necessary.

A final, second round of training was performed to further refine $n^{th}$ model 520n for the ultimate purpose of predicting side chain types at an interface, rather than arbitrary positions within one or more molecules. Accordingly, a second, interface specific training dataset 540 was created, this time using graph representations of complexes where masked side chain components were restricted to interface nodes. Training dataset 540 was used to train $n^{th}$ model 520n, to create a final model 550.

FIG. 5B illustrates, schematically, how each block may receive, as input, various types of feature vectors, including known and unknown features, and be used to predict new distributions, similar to the approach described above with respect to FIGS. 4C and 4D. In FIG. 5B, each node representation includes amino acid (AA) encoding indicating type of amino acid (in green) and structural descriptors (in blue). The illustrative process for predicting new amino acid distributions is iterative. The distributions of amino acids are initialized from the empirical distribution in the molecule (i=0), where the graph is composed of a set of known and unknown nodes labels. During each pass through the machine learning architecture detailed in FIG. 5C (the "AH bloc"), (i to i+1), the distributions are updated, with the distributions of known nodes reset as in the input. The process may be repeated as much as desired.

FIG. 5C shows a schematic of an illustrative architecture used to create a block ("AH bloc") used in the present example. Other architectures, using different types of layers, organizations, and the like, are also contemplated. FIG. 5C shows the overall process flow 560 and details of the "AH bloc" architecture 570, 580 depicted in FIGS. 5B and 5C and used in the examples whose results are shown below.

C.ii Results

Table 1 below shows overall performance of the approach for classifying amino acid side chain types over a full molecule test set, created analogously to full molecule training dataset 510 (i.e., not necessarily restricted to an interface specific test set), described above with respect to FIGS. 5A-5C. Overall performance may be quantified using, among other things, an identity score and a similarity score. Identity score measures the fraction of predicted side chain types that were identical to the ground truth, while similarity score accounts for similarities between certain types of amino acids (as determined according to the BLOSUM 62 matrix) (e.g., while a predicted side chain type might not be identical to the ground truth, it may be a type that would work just as well in the structure).

TABLE 1

Overall Performance Evaluated on a Full Molecule Test Dataset

Overall performances

Identity: 0.47438593137723406

Similarity: 0.6653624677434771

Total number of predictions: 167408

Total number of molecules: 835

Table 2 displays performance metrics evaluated on a full molecule test dataset, broken down by side chain type.

TABLE 2

Individual Side Chain Performance Evaluated on a Full Molecule Test Dataset

|  | precision | recall | f1-score | support | pred | AUC | accuracy |
|---|---|---|---|---|---|---|---|
| GLN | 0.199264 | 0.141911 | 0.165767 | 6490.0 | 4622.0 | 0.808566 | 0.141911 |
| MET | 0.135765 | 0.221763 | 0.168421 | 3391.0 | 5539.0 | 0.802935 | 0.221763 |
| LEU | 0.632664 | 0.584545 | 0.607653 | 16435.0 | 15185.0 | 0.926520 | 0.584545 |
| VAL | 0.553306 | 0.557207 | 0.555250 | 11773.0 | 11856.0 | 0.941588 | 0.557207 |
| SER | 0.495857 | 0.348429 | 0.409271 | 10820.0 | 7603.0 | 0.874407 | 0.348429 |
| GLY | 0.992451 | 0.998553 | 0.995493 | 11060.0 | 11128.0 | 0.999976 | 0.998553 |
| THR | 0.456399 | 0.501720 | 0.477987 | 9013.0 | 9908.0 | 0.905942 | 0.501720 |
| GLU | 0.323074 | 0.320018 | 0.321539 | 11415.0 | 11307.0 | 0.855357 | 0.320018 |
| LYS | 0.269124 | 0.252146 | 0.260359 | 10018.0 | 9386.0 | 0.848505 | 0.252146 |
| PRO | 0.950006 | 0.984458 | 0.966925 | 7528.0 | 7801.0 | 0.999760 | 0.984458 |
| ILE | 0.471653 | 0.601909 | 0.528879 | 9744.0 | 12435.0 | 0.945871 | 0.601909 |
| CYS | 0.329253 | 0.562566 | 0.415391 | 2821.0 | 4820.0 | 0.903031 | 0.562566 |
| TYR | 0.327718 | 0.316527 | 0.322026 | 6208.0 | 5996.0 | 0.899680 | 0.316527 |
| PHE | 0.436844 | 0.388787 | 0.411417 | 7063.0 | 6286.0 | 0.916806 | 0.388787 |
| TRP | 0.231514 | 0.233778 | 0.232640 | 2250.0 | 2272.0 | 0.875576 | 0.233778 |
| ARG | 0.263850 | 0.238223 | 0.250382 | 8597.0 | 7762.0 | 0.837169 | 0.238223 |
| ASP | 0.454535 | 0.421467 | 0.437377 | 9773.0 | 9062.0 | 0.904510 | 0.421467 |
| ALA | 0.587853 | 0.536839 | 0.561189 | 12134.0 | 11081.0 | 0.920568 | 0.536839 |
| ASN | 0.344873 | 0.351297 | 0.348055 | 7515.0 | 7655.0 | 0.877052 | 0.351297 |
| HIS | 0.163275 | 0.264017 | 0.201770 | 3799.0 | 6143.0 | 0.826591 | 0.264017 |
| avg/total | 0.481851 | 0.475308 | 0.475714 | 167847.0 | 167847.0 | 0.919044 | 0.475308 |

Figure 6A:
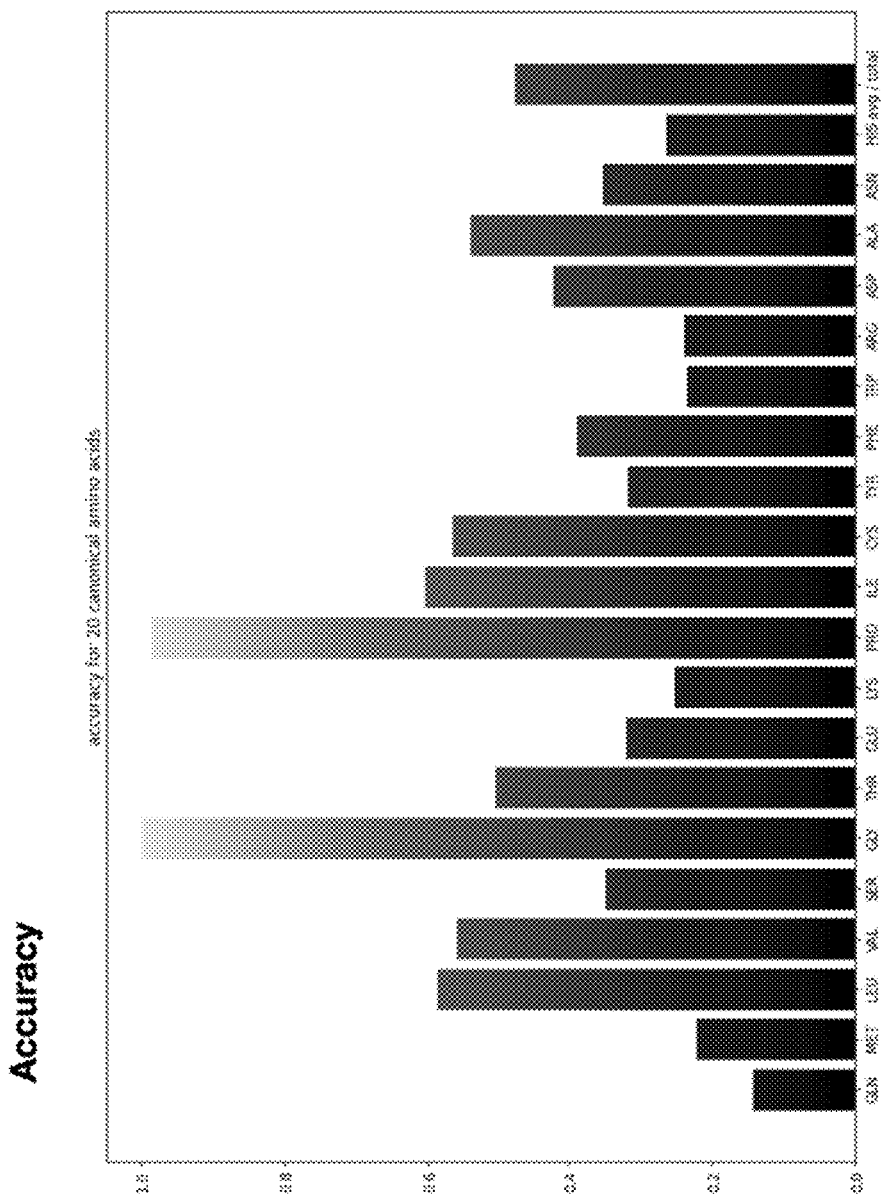
FIG. 6A is bar graph showing accuracy of predictions for 20 amino acid side chain types evaluated using a full molecule test dataset.
Figure 6B:
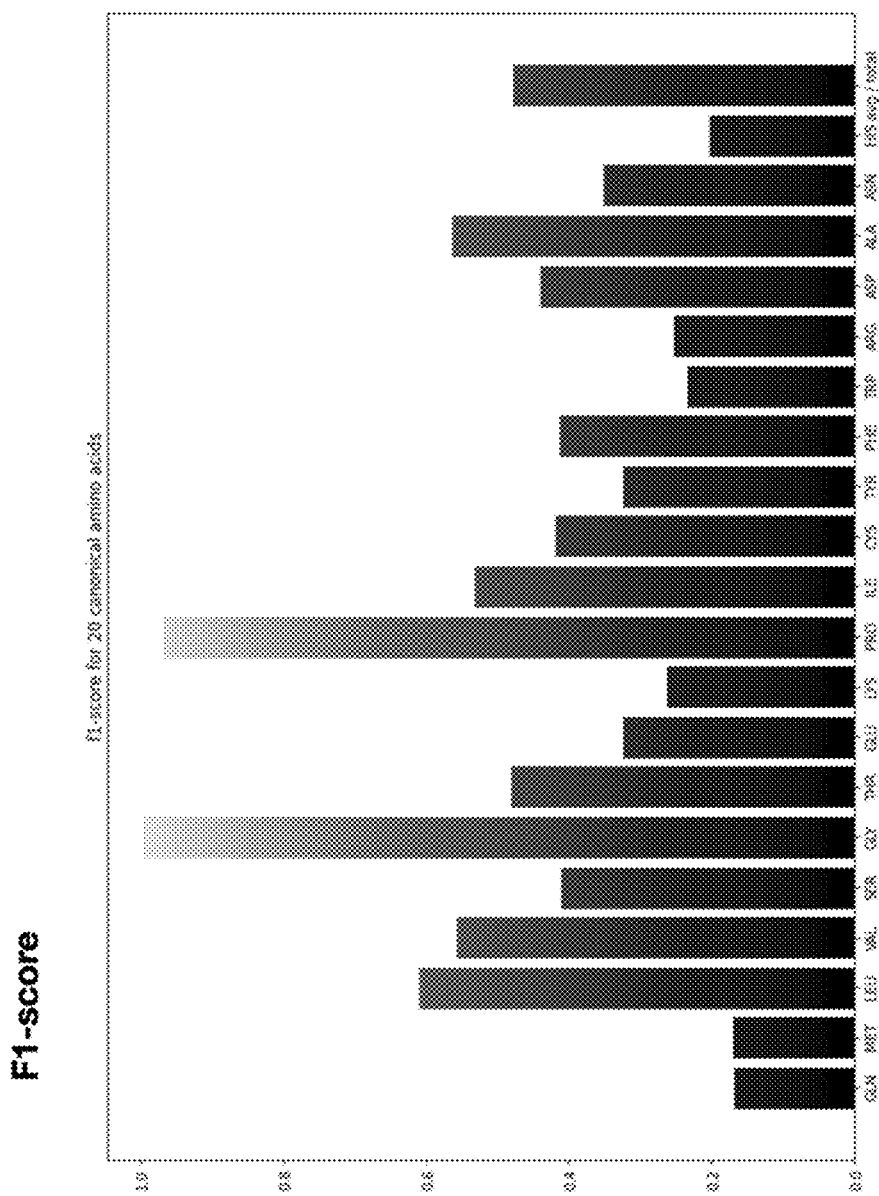
FIG. 6B is bar graph showing F1-scores for predictions for 20 amino acid side chain types evaluated using a full molecule test dataset.
Figure 6C:
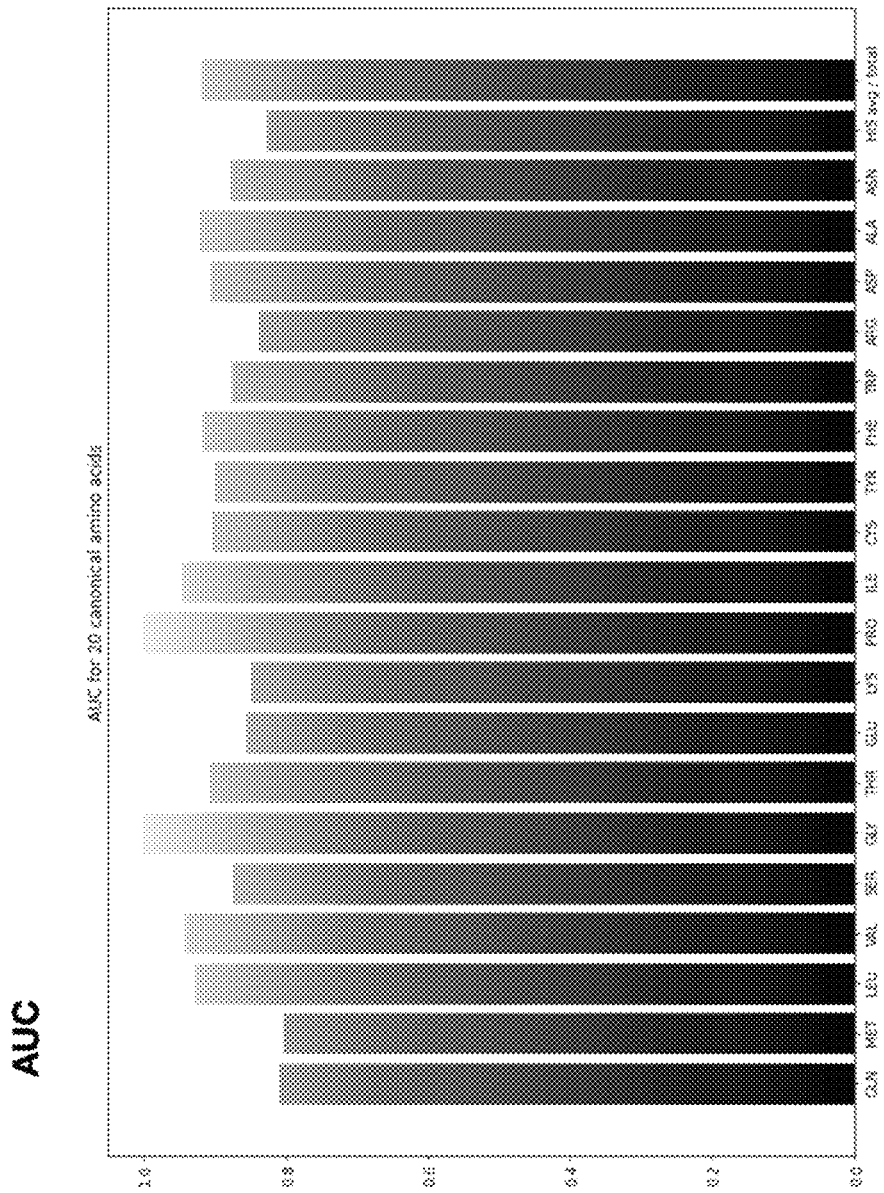
FIG. 6C is bar graph showing Area Under the Curve (AUC) values for predictions for 20 amino acid side chain types evaluated using a full molecule test dataset.

FIGS. 6A-C show accuracy, F1-score, and AUC metrics for predictions of each particular side chain type (20 canonical amino acids) obtained using the graph neural network approach of the present example.

Performance was also evaluated using an interface specific test data set, created analogously to interface specific training dataset 540. The interface specific test dataset allowed performance for predicting amino acid side chain types for unknown interface nodes to be evaluated.

Tables 3 and 4 below shows overall performance of the approach for classifying amino acid side chain types over the interface specific test set, and broken down by particular side chain type, respectively, conveying the same information as in Tables 1 and 2 above, but for the interface specific test dataset).

TABLE 3

Overall Performance Evaluated on an Interface Specific Test Dataset

Overall performances

Identity: 0.4412931105215655

Similarity: 0.6527090227825945

Total number of predictions: 36563

Total number of interfaces: 835

TABLE 4

Individual Side Chain Performance Evaluated on an Interface Specific Test Dataset

|  | precision | recall | f1-score | support | pred | AUC | accuracy |
|---|---|---|---|---|---|---|---|
| GLN | 0.181713 | 0.110098 | 0.137118 | 1426.0 | 864.0 | 0.791252 | 0.110098 |
| MET | 0.140365 | 0.204624 | 0.166510 | 865.0 | 1261.0 | 0.807995 | 0.204624 |
| LEU | 0.515658 | 0.563605 | 0.538566 | 3506.0 | 3832.0 | 0.897962 | 0.563605 |
| VAL | 0.520308 | 0.427365 | 0.469279 | 2368.0 | 1945.0 | 0.921030 | 0.427365 |
| SER | 0.474289 | 0.308370 | 0.372270 | 2559.0 | 1653.0 | 0.851905 | 0.306370 |
| GLY | 0.991312 | 0.996782 | 0.994039 | 2175.0 | 2187.0 | 0.999880 | 0.996782 |
| THR | 0.489415 | 0.383228 | 0.429861 | 2051.0 | 1606.0 | 0.877177 | 0.383228 |
| GLU | 0.278485 | 0.347461 | 0.309173 | 2265.0 | 2826.0 | 0.841155 | 0.347461 |
| LYS | 0.209687 | 0.386424 | 0.271856 | 1871.0 | 3448.0 | 0.847177 | 0.386424 |
| PRO | 0.953555 | 0.967986 | 0.960716 | 1718.0 | 1744.0 | 0.998978 | 0.967986 |
| ILE | 0.447398 | 0.566888 | 0.500105 | 2108.0 | 2671.0 | 0.936182 | 0.566888 |
| CYS | 0.399746 | 0.519802 | 0.451937 | 606.0 | 788.0 | 0.891913 | 0.519802 |
| TYR | 0.287647 | 0.314874 | 0.300646 | 1553.0 | 1700.0 | 0.881837 | 0.314874 |
| PHE | 0.479428 | 0.321729 | 0.385057 | 1666.0 | 1118.0 | 0.907990 | 0.321729 |
| TRP | 0.177072 | 0.289963 | 0.219873 | 538.0 | 881.0 | 0.878418 | 0.289963 |
| ARG | 0.300469 | 0.181818 | 0.226549 | 2112.0 | 1278.0 | 0.834137 | 0.181818 |
| ASP | 0.463065 | 0.396975 | 0.427481 | 2116.0 | 1814.0 | 0.891215 | 0.396975 |
| ALA | 0.507514 | 0.527433 | 0.517282 | 2497.0 | 2595.0 | 0.900312 | 0.527433 |
| ASK | 0.318699 | 0.298552 | 0.307358 | 1658.0 | 1563.0 | 0.845206 | 0.298552 |
| HIS | 0.221800 | 0.193370 | 0.206612 | 905.0 | 789.0 | 0.822973 | 0.193370 |
| avg/total | 0.453710 | 0.441293 | 0.440905 | 36563.0 | 36563.0 | 0.903696 | 0.441293 |

Figure 7A:
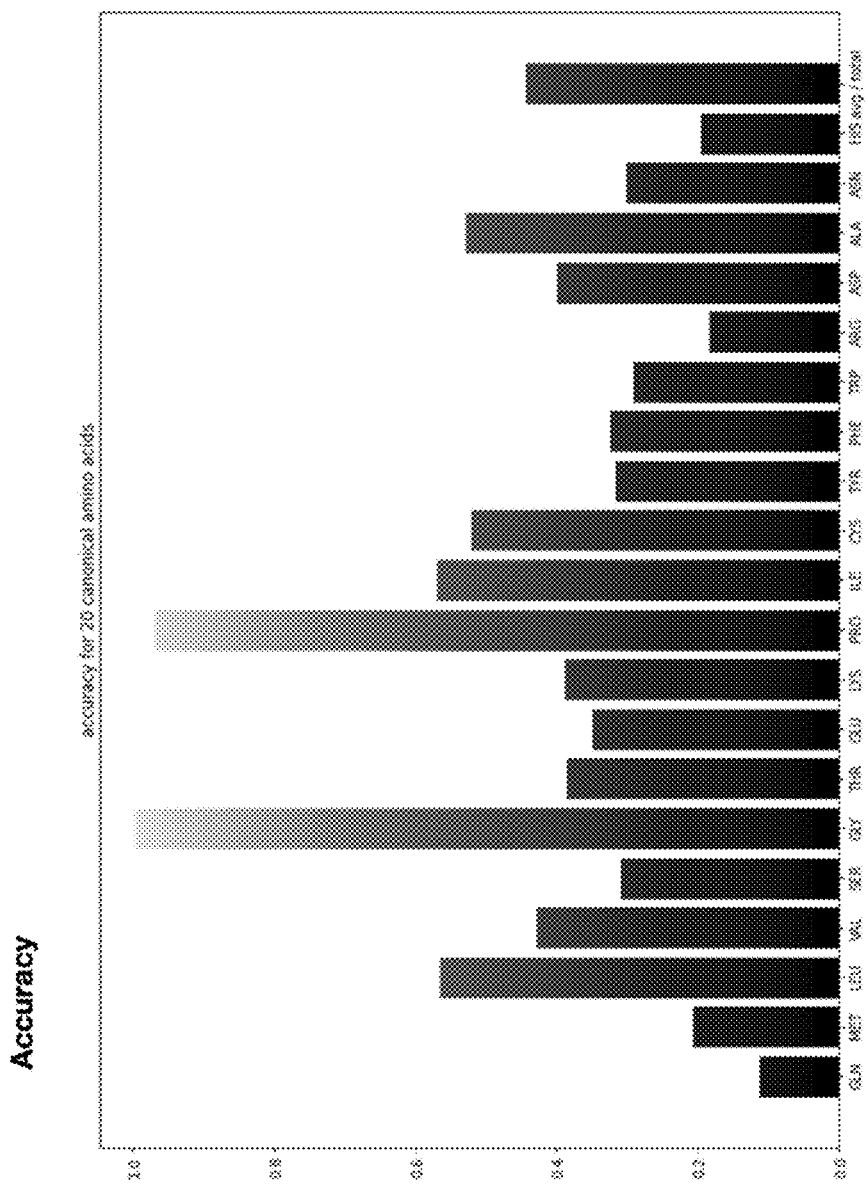
FIG. 7A is bar graph showing accuracy of predictions for 20 amino acid side chain types evaluated using an interface specific test dataset.
Figure 7B:
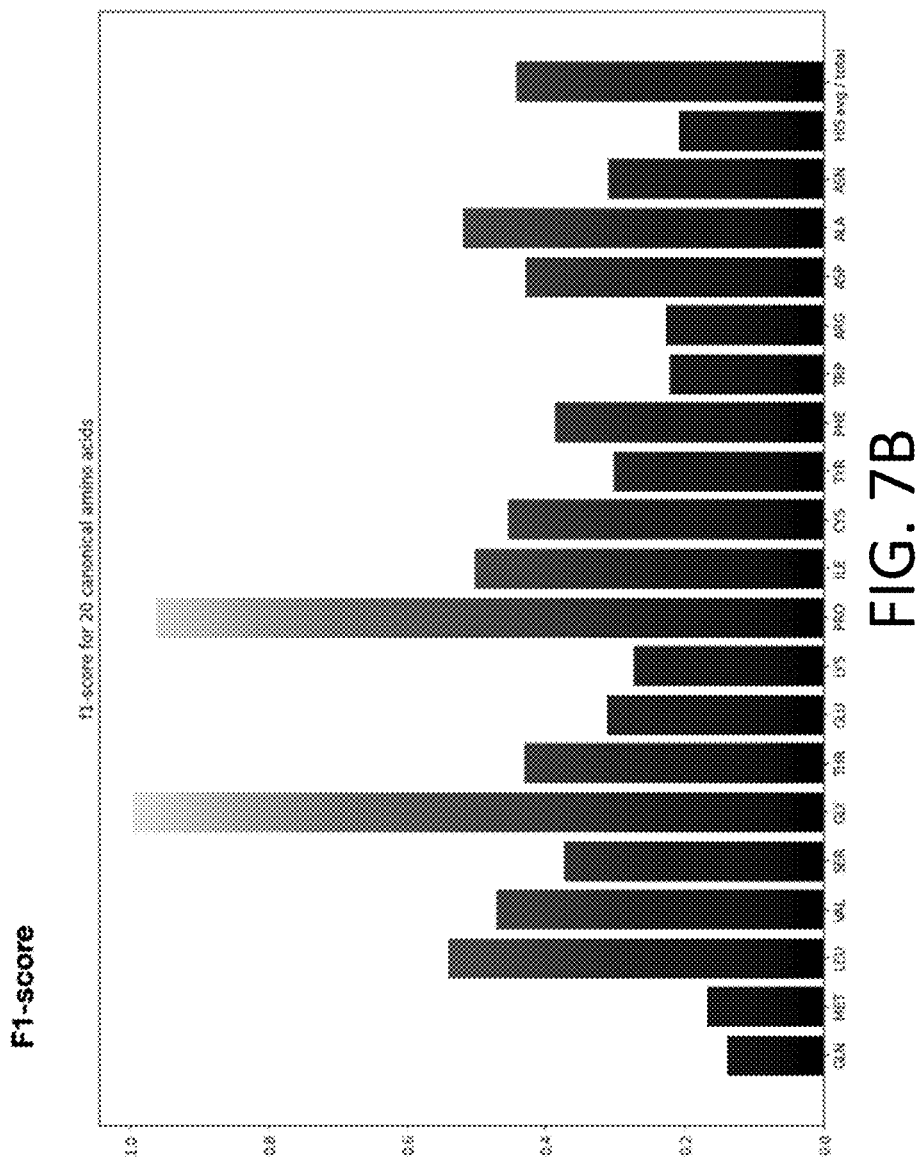
FIG. 7B is bar graph showing F1-scores for predictions for 20 amino acid side chain types evaluated using an interface specific test dataset.
Figure 7C:
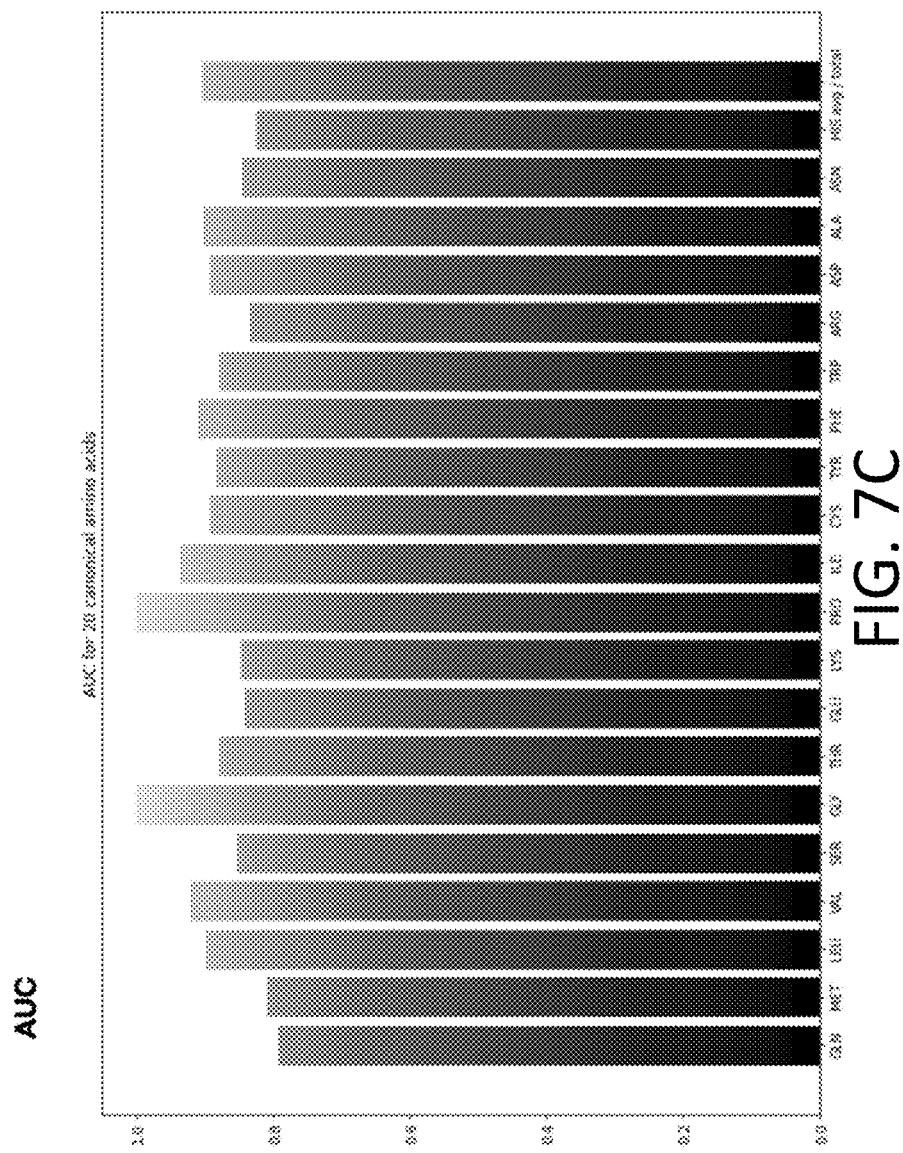
FIG. 7C is bar graph showing Area Under the Curve (AUC) values for predictions for 20 amino acid side chain types evaluated using an interface specific test dataset.

FIGS. 7A-C are analogous to FIGS. 6A-C, but show results obtained for predictions over the interface specific dataset.

These results, in particular the area under the curve (AUC) metrics shown in FIGS. 6C and 7C demonstrate accurate performance of the approaches described herein.

D. Computer System and Network Environment

Figure 8:
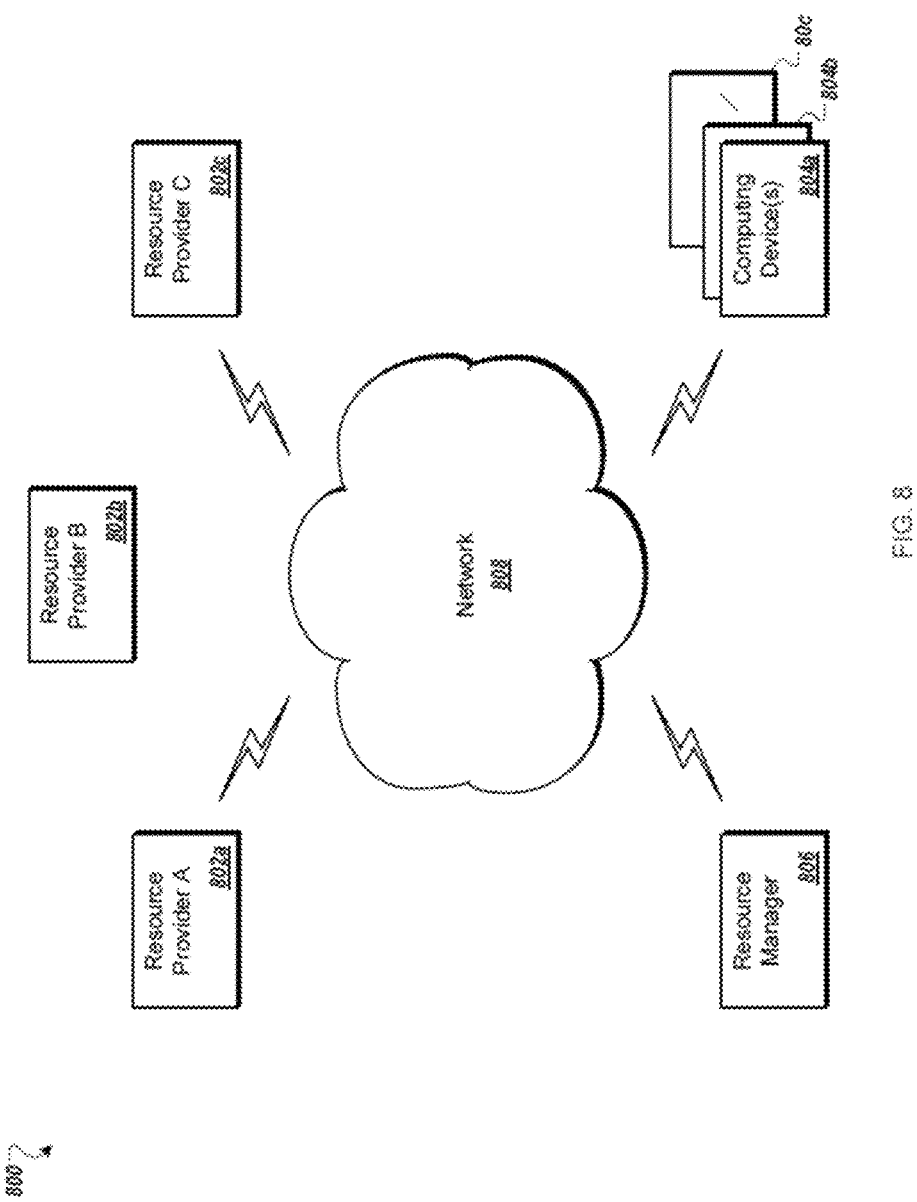
FIG. 8 is a block diagram of an exemplary cloud computing environment, used in certain embodiments.

Turning to FIG. 8, an implementation of a network environment 800 for use in providing systems, methods, and architectures as described herein is shown and described. In brief overview, referring now to FIG. 8, a block diagram of an exemplary cloud computing environment 800 is shown and described. The cloud computing environment 800 may include one or more resource providers 802a, 802b, 802c (collectively, 802). Each resource provider 802 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 802 may be connected to any other resource provider 802 in the cloud computing environment 800. In some implementations, the resource providers 802 may be connected over a computer network 808. Each resource provider 802 may be connected to one or more computing device 804a, 804b, 804c (collectively, 804), over the computer network 808.

The cloud computing environment 800 may include a resource manager 806. The resource manager 806 may be connected to the resource providers 802 and the computing devices 804 over the computer network 808. In some implementations, the resource manager 806 may facilitate the provision of computing resources by one or more resource providers 802 to one or more computing devices 804. The resource manager 806 may receive a request for a computing resource from a particular computing device 804. The resource manager 806 may identify one or more resource providers 802 capable of providing the computing resource requested by the computing device 804. The resource manager 806 may select a resource provider 802 to provide the computing resource. The resource manager 806 may facilitate a connection between the resource provider 802 and a particular computing device 804. In some implementations, the resource manager 806 may establish a connection between a particular resource provider 802 and a particular computing device 804. In some implementations, the resource manager 806 may redirect a particular computing device 804 to a particular resource provider 802 with the requested computing resource.

Figure 9:
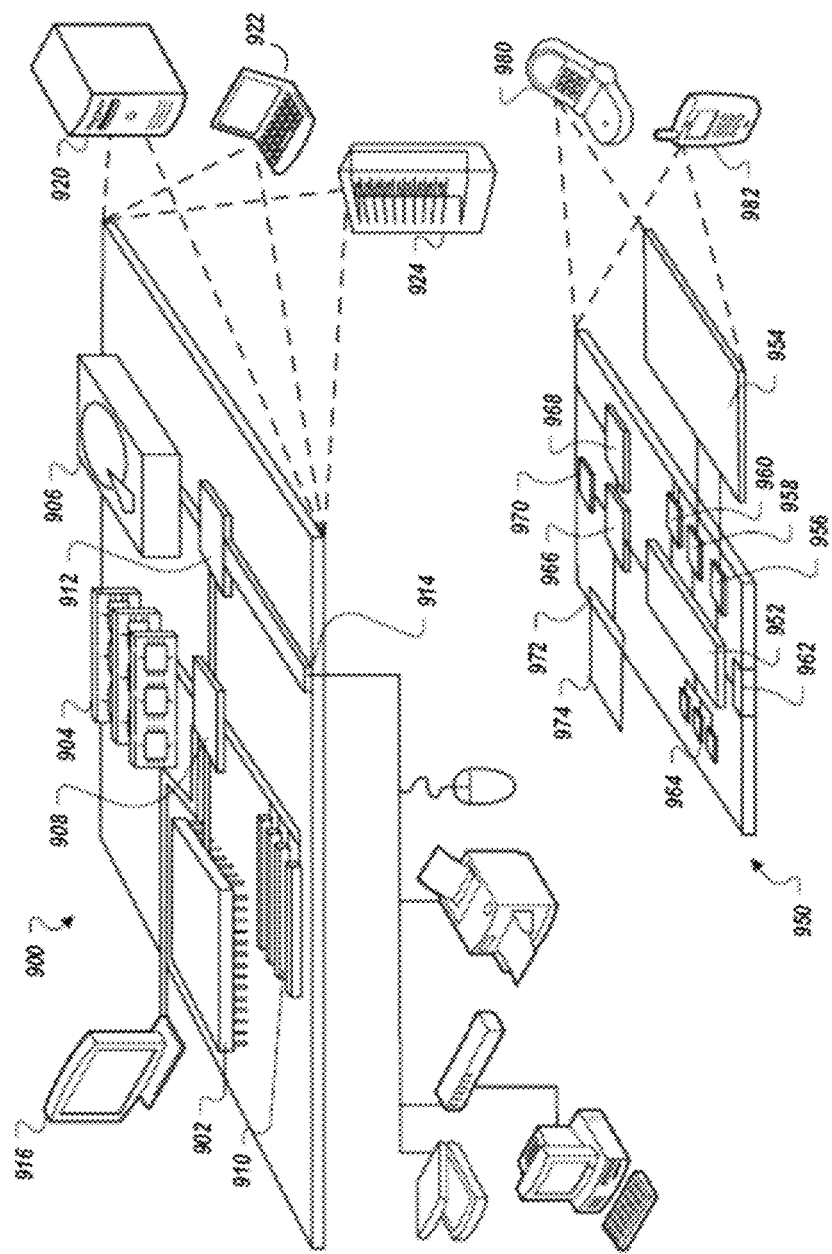
FIG. 9 is a block diagram of an example computing device and an example mobile computing device, used in certain embodiments.

FIG. 9 shows an example of a computing device 900 and a mobile computing device 950 that can be used to implement the techniques described in this disclosure. The computing device 900 is intended to represent various forms of digital computers, such as laptops, desktops, workstations, personal digital assistants, servers, blade servers, mainframes, and other appropriate computers. The mobile computing device 950 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 900 includes a processor 902, a memory 904, a storage device 906, a high-speed interface 908 connecting to the memory 904 and multiple high-speed expansion ports 910, and a low-speed interface 912 connecting to a low-speed expansion port 914 and the storage device 906. Each of the processor 902, the memory 904, the storage device 906, the high-speed interface 908, the high-speed expansion ports 910, and the low-speed interface 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as a display 916 coupled to the high-speed interface 908. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 904 stores information within the computing device 900. In some implementations, the memory 904 is a volatile memory unit or units. In some implementations, the memory 904 is a non-volatile memory unit or units. The memory 904 may also be another form of computer-readable medium, such as a magnetic or optical disk.

The storage device 906 is capable of providing mass storage for the computing device 900. In some implementations, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 902), perform one or more methods, such as those described above. The instructions can also be stored by one or more storage devices such as computer- or machine-readable mediums (for example, the memory 904, the storage device 906, or memory on the processor 902).

The high-speed interface 908 manages bandwidth-intensive operations for the computing device 900, while the low-speed interface 912 manages lower bandwidth-intensive operations. Such allocation of functions is an example only. In some implementations, the high-speed interface 908 is coupled to the memory 904, the display 916 (e.g., through a graphics processor or accelerator), and to the high-speed expansion ports 910, which may accept various expansion cards (not shown). In the implementation, the low-speed interface 912 is coupled to the storage device 906 and the low-speed expansion port 914. The low-speed expansion port 914, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. In addition, it may be implemented in a personal computer such as a laptop computer 922. It may also be implemented as part of a rack server system 924. Alternatively, components from the computing device 900 may be combined with other components in a mobile device (not shown), such as a mobile computing device 950. Each of such devices may contain one or more of the computing device 900 and the mobile computing device 950, and an entire system may be made up of multiple computing devices communicating with each other.

The mobile computing device 950 includes a processor 952, a memory 964, an input/output device such as a display 954, a communication interface 966, and a transceiver 968, among other components. The mobile computing device 950 may also be provided with a storage device, such as a micro-drive or other device, to provide additional storage. Each of the processor 952, the memory 964, the display 954, the communication interface 966, and the transceiver 968, are interconnected using various buses, and several of the components may be mounted on a common motherboard or in other manners as appropriate.

The processor 952 can execute instructions within the mobile computing device 950, including instructions stored in the memory 964. The processor 952 may be implemented as a chipset of chips that include separate and multiple analog and digital processors. The processor 952 may provide, for example, for coordination of the other components of the mobile computing device 950, such as control of user interfaces, applications run by the mobile computing device 950, and wireless communication by the mobile computing device 950.

The processor 952 may communicate with a user through a control interface 958 and a display interface 956 coupled to the display 954. The display 954 may be, for example, a TFT (Thin-Film-Transistor Liquid Crystal Display) display or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may provide communication with the processor 952, so as to enable near area communication of the mobile computing device 950 with other devices. The external interface 962 may provide, for example, for wired communication in some implementations, or for wireless communication in other implementations, and multiple interfaces may also be used.

The memory 964 stores information within the mobile computing device 950. The memory 964 can be implemented as one or more of a computer-readable medium or media, a volatile memory unit or units, or a non-volatile memory unit or units. An expansion memory 974 may also be provided and connected to the mobile computing device 950 through an expansion interface 972, which may include, for example, a SIMM (Single In Line Memory Module) card interface. The expansion memory 974 may provide extra storage space for the mobile computing device 950, or may also store applications or other information for the mobile computing device 950. Specifically, the expansion memory 974 may include instructions to carry out or supplement the processes described above, and may include secure information also. Thus, for example, the expansion memory 974 may be provide as a security module for the mobile computing device 950, and may be programmed with instructions that permit secure use of the mobile computing device 950. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 952), perform one or more methods, such as those described above. The instructions can also be stored by one or more storage devices, such as one or more computer- or machine-readable mediums (for example, the memory 964, the expansion memory 974, or memory on the processor 952). In some implementations, the instructions can be received in a propagated signal, for example, over the transceiver 968 or the external interface 962.

The mobile computing device 950 may communicate wirelessly through the communication interface 966, which may include digital signal processing circuitry where necessary. The communication interface 966 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 968 using a radio-frequency. In addition, short-range communication may occur, such as using a Bluetooth®, Wi-Fi™, or other such transceiver (not shown). In addition, a GPS (Global Positioning System) receiver module 970 may provide additional navigation- and location-related wireless data to the mobile computing device 950, which may be used as appropriate by applications running on the mobile computing device 950.

The mobile computing device 950 may also communicate audibly using an audio codec 960, which may receive spoken information from a user and convert it to usable digital information. The audio codec 960 may likewise generate audible sound for a user, such as through a speaker, e.g., in a handset of the mobile computing device 950. Such sound may include sound from voice telephone calls, may include recorded sound (e.g., voice messages, music files, etc.) and may also include sound generated by applications operating on the mobile computing device 950.

The mobile computing device 950 may be implemented in a number of different forms, as shown in the figure. For example, it may be implemented as a cellular telephone 980. It may also be implemented as part of a smart-phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Actions associated with implementing the systems may be performed by one or more programmable processors executing one or more computer programs. All or part of the systems may be implemented as special purpose logic circuitry, for example, a field programmable gate array (FPGA) or an application-specific integrated circuit (ASIC), or both. All or part of the systems may also be implemented as special purpose logic circuitry, for example, a specially designed (or configured) central processing unit (CPU), conventional central processing units (CPU) a graphics processing unit (GPU), and/or a tensor processing unit (TPU).

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for the in-silico design of an amino acid interface of a biologic for binding to a target, the method comprising:
   (a) receiving, by a processor of a computing device, an initial scaffold-target complex graph comprising a graph representation of at least a portion of a biologic complex comprising the target and a peptide backbone of the in-progress custom biologic, the initial scaffold-target complex graph comprising:
      a target graph representing at least a portion of the target; and
      a scaffold graph representing at least a portion of the peptide backbone of the in-progress custom biologic, the scaffold graph comprising a plurality of scaffold nodes, a subset of which are unknown interface nodes, wherein each of said unknown interface nodes:
         (i) represents a particular amino acid interface site, along the peptide backbone of the in-progress custom biologic, that is located in proximity to one or more amino acids of the target, and
         (ii) has a corresponding node feature vector comprising a side chain type component vector populated with one or more masking values, thereby representing an unknown, to-be determined, amino acid side chain;
   (b) generating, by the processor, using a machine learning model, one or more likelihood graphs based on the initial scaffold-target complex graph, each of the one or more likelihood graphs comprising a plurality of nodes, a subset of which are classified interface nodes, each of which:
      (i) corresponds to a particular unknown interface node of the scaffold graph and represents a same particular interface site along the peptide backbone of the in-progress custom biologic as the corresponding particular interface node, and
      (ii) has a corresponding node feature vector comprising a side chain component vector populated with one or more likelihood values;
   (c) using, by the processor, the one or more likelihood graphs to determine a predicted interface comprising, for each interface site, an identification of a particular amino acid side chain type; and,
   (d) providing the predicted interface for use in designing the amino acid interface of the in-progress custom biologic and/or using the predicted interface to design the amino acid interface of the in-progress custom biologic.

2. The method of claim 1, wherein the target graph comprises a plurality of target nodes, each representing a particular amino acid site of the target and having a corresponding node feature vector comprising one or more constituent vectors, each constituent vector representing a particular feature of the particular amino acid site.

3. The method of claim 2, wherein, for each node feature vector of a target node, the one or more constituent vectors comprise one or more members selected from the group consisting of:
   a side chain type, representing a particular type of amino acid side chain;
   a local backbone geometry; and
   a side chain geometry.

4. The method of claim 2, wherein the node feature vectors and/or edge feature vectors of the target graph are invariant with respect to three-dimensional translation and/or rotation of the target.

5. The method of claim 2, wherein, for each node feature vector of a target node, at least a subset of the one or more constituent vectors comprise absolute coordinate values of one or more atoms of the particular amino acid site represented by the target node.

6. The method of claim 1, wherein the target graph comprises a plurality of target edges, each associated with two particular target nodes and having a corresponding edge feature vector comprising one or more constituent vectors representing a relative position and/or orientation of two amino acid sites represented by the two particular target nodes.

7. The method of claim 1, wherein each of the plurality of scaffold nodes of the scaffold graph represents a particular amino acid site along the peptide backbone of the in-progress custom biologic and has a corresponding node feature vector comprising one or more constituent vectors, each constituent vector representing a particular feature of the particular amino acid site.

8. The method of claim 7, wherein, for each node feature vector of a scaffold node, the one or more constituent vectors comprise one or more members selected from the group consisting of:
 a side chain type, representing a particular type of amino acid side chain;
 a local backbone geometry; and
 a side chain geometry.

9. The method of claim 7, wherein the node feature vectors and/or edge feature vectors of the scaffold graph are invariant with respect to three-dimensional translation and/or rotation of the peptide backbone of the in-progress custom biologic.

10. The method of claim 7, wherein, for each node feature vector of a target node, at least a subset of the one or more constituent vectors comprise absolute coordinate values of one or more atoms of the particular amino acid site represented by the target node.

11. The method of claim 1, wherein the scaffold graph comprises a plurality of scaffold edges, each associated with two particular scaffold nodes and having a corresponding edge feature vector comprising one or more constituent vectors representing a relative position and/or orientation of two amino acid sites represented by the two particular scaffold nodes, and wherein the initial scaffold-target complex graph comprises a plurality of scaffold-target edges, each corresponding to a particular scaffold node and a particular target node and having a corresponding edge feature vector comprising one or more constituent vectors representing a relative position and/or orientation of two amino acid sites represented by the particular scaffold node and the particular target node.

12. The method of claim 1, wherein a subset of the scaffold nodes are known scaffold nodes, each having a node feature vector comprising a known side chain component representing an amino acid side chain type.

13. The method of claim 1, wherein the machine learning model is or comprises a graph neural network.

14. The method of claim 1, wherein step (b) comprises generating a plurality of likelihood graphs in an iterative fashion by:
 in a first iteration, using the initial scaffold-target complex graph as an initial input to generate an initial likelihood graph;
 in a second, subsequent iteration, using the initial likelihood graph and/or an initial interface prediction based thereon, as input to the machine learning model, to generate a refined likelihood graph and/or a refined interface prediction based thereon; and
 repeatedly using the refined likelihood graph and/or refined interface prediction generated by the machine learning model at one iteration as input to the machine learning model for a subsequent iteration, thereby repeatedly refining the likelihood graph and or an interface prediction based thereon.

15. The method of claim 1, wherein each of the one or more likelihood values represents a likelihood that a side chain at the particular amino acid site is of a particular amino acid type.

16. The method of claim 1, wherein:
 (i) the target is a protein or peptide and the target graph is or comprises a representation of at least a portion of a 3D protein and/or peptide structure of the target; and
 (ii) the in-progress custom biologic is a partially determined protein or peptide having a particular peptide backbone structure and an as-yet to be determined amino acid interface for binding to the target, and the scaffold graph is or comprises a representation of a 3D protein and/or peptide structure of the particular peptide backbone.

17. A system for the in-silico design of an amino acid interface of a biologic for binding to a target, the system comprising:
 a processor of a computing device; and
 a memory having instructions stored thereon, wherein the instructions, when executed by the processor, cause the processor to:
 (a) receive an initial scaffold-target complex graph comprising a graph representation of at least a portion of a biologic complex comprising the target and a peptide backbone of the in-progress custom biologic, the initial scaffold-target complex graph comprising:
  a target graph representing at least a portion of the target; and
  a scaffold graph representing at least a portion of the peptide backbone of the in-progress custom biologic, the scaffold graph comprising a plurality of scaffold nodes, a subset of which are unknown interface nodes, wherein each of said unknown interface nodes:
   (i) represents a particular amino acid interface site, along the peptide backbone of the in-progress custom biologic, that is located in proximity to one or more amino acids of the target, and
   (ii) has a corresponding node feature vector comprising a side chain type component vector populated with one or more masking values, thereby representing an unknown, to-be determined, amino acid side chain;
 (b) generate, using a machine learning model, one or more likelihood graphs based on the initial scaffold-target complex graph, each of the one or more likelihood graphs comprising a plurality of nodes, a subset of which are classified interface nodes, each of which:
  (i) corresponds to a particular unknown interface node of the scaffold graph and represents a same particular interface site along the peptide backbone of the in-progress custom biologic as the corresponding particular interface node, and
  (ii) has a corresponding node feature vector comprising a side chain component vector populated with on or more likelihood values;
 (c) use the one or more likelihood graphs to determine a predicted interface comprising, for each interface site, an identification of a particular amino acid side chain type; and
 (d) provide the predicted interface for use in designing the amino acid interface of the in-progress custom biologic and/or using the predicted interface to design the amino acid interface of the in-progress custom biologic.

18. The system of claim 17, wherein the target graph comprises a plurality of target nodes, each representing a particular amino acid site of the target and having a corresponding node feature vector comprising one or more constituent vectors, each constituent vector representing a particular feature of the particular amino acid site.

19. The system of claim 18, wherein, for each node feature vector of a target node, the one or more constituent vectors comprise one or more members selected from the group consisting of:
 a side chain type, representing a particular type of amino acid side chain;
 a local backbone geometry; and
 a side chain geometry.

20. The system of claim 18, wherein the node feature vectors and/or edge feature vectors of the target graph are invariant with respect to three-dimensional translation and/or rotation of the target.

21. The system of claim 18, wherein, for each node feature vector of a target node, at least a subset of the one or more constituent vectors comprise an absolute of one or more atoms of the particular amino acid site represented by the target node.

22. The system of claim 17, wherein the target graph comprises a plurality of target edges, each associated with two particular target nodes and having a corresponding edge feature vector comprising one or more constituent vectors representing a relative position and/or orientation of two amino acid sites represented by the two particular target nodes.

23. The system of claim 17, wherein each of the plurality of scaffold nodes of the scaffold graph represents a particular amino acid site along the peptide backbone of the in-progress custom biologic and has a corresponding node feature vector comprising one or more constituent vectors, each constituent vector representing a particular feature of the particular amino acid site.

24. The system of claim 23, wherein, for each node feature vector of a scaffold node, the one or more constituent vectors comprise one or more members selected from the group consisting of:
 a side chain type, representing a particular type of amino acid side chain;
 a local backbone geometry; and
 a side chain geometry.

25. The system of claim 23, wherein the node feature vectors and/or edge feature vectors of the scaffold graph are invariant with respect to three-dimensional translation and/or rotation of the peptide backbone of the in-progress custom biologic.

26. The system of claim 23, wherein, for each node feature vector of a target node, at least a subset of the one or more constituent vectors comprise absolute coordinate values of one or more atoms of the particular amino acid site represented by the target node.

27. The system of claim 17, wherein the scaffold graph comprises a plurality of scaffold edges, each associated with two particular scaffold nodes and having a corresponding edge feature vector comprising one or more constituent vectors representing a relative position and/or orientation of two amino acid sites represented by the two particular scaffold nodes, and wherein the initial scaffold-target complex graph comprises a plurality of scaffold-target edges, each corresponding to a particular scaffold node and a particular target node and having a corresponding edge feature vector comprising one or more constituent vectors representing a relative position and/or orientation of two amino acid sites represented by the particular scaffold node and the particular target node.

28. The system of claim 17, wherein a subset of the scaffold nodes are known scaffold nodes, each having a node feature vector comprising a known side chain component representing an amino acid side chain type.

29. The system of claim 17, wherein the machine learning model is or comprises a graph neural network.

30. The system of claim 17, wherein the instructions, when executed by the processor, cause the processor to, in step (b), generate a plurality of likelihood graphs in an iterative fashion by:
 in a first iteration, use the initial scaffold-target complex graph as an initial input to generate an initial likelihood graph;
 in a second, subsequent iteration, use the initial likelihood graph and/or an initial interface prediction based thereon, as input to the machine learning model, to generate a refined likelihood graph and/or a refined interface prediction based thereon; and
 repeatedly use the refined likelihood graph and/or refined interface prediction generated by the machine learning model at one iteration as input to the machine learning model for a subsequent iteration, thereby repeatedly refining the likelihood graph and or an interface prediction based thereon.

* * * * *